United States Patent
Arnaud et al.

(10) Patent No.: US 10,905,640 B2
(45) Date of Patent: Feb. 2, 2021

(54) COSMETIC COMPOSITION CONTAINING A POLYMER COMPRISING A CARBOSILOXANE DENDRIMER UNIT

(71) Applicant: L'OREAL, Paris (FR)

(72) Inventors: Pascal Arnaud, L'Hay les Roses (FR); Euriel Clavel, Paris (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/971,178

(22) Filed: May 4, 2018

(65) Prior Publication Data

US 2018/0250206 A1 Sep. 6, 2018
US 2020/0360248 A9 Nov. 19, 2020

Related U.S. Application Data

(63) Continuation of application No. 13/056,056, filed as application No. PCT/IB2009/053831 on Sep. 2, 2009, now Pat. No. 10,646,421.

(60) Provisional application No. 61/098,806, filed on Sep. 22, 2008.

(30) Foreign Application Priority Data

Sep. 4, 2008 (FR) .................................. 08 55943

(51) Int. Cl.
*A61Q 1/02* (2006.01)
*A61K 8/25* (2006.01)
*A61K 8/91* (2006.01)

(52) U.S. Cl.
CPC .................. *A61K 8/25* (2013.01); *A61K 8/91* (2013.01); *A61Q 1/02* (2013.01)

(58) Field of Classification Search
None
See application file for complete search history.

(56) References Cited

U.S. PATENT DOCUMENTS

| 5,130,390 | A | 7/1992 | Weber et al. |
| 6,887,859 | B2 | 5/2005 | Clapp et al. |
| 2002/0028184 | A1 | 3/2002 | Sunkel et al. |
| 2003/0003059 | A1 | 1/2003 | Dana |
| 2004/0175338 | A1 | 9/2004 | Filippi et al. |
| 2006/0074187 | A1 | 4/2006 | Stark et al. |
| 2008/0003195 | A1 | 1/2008 | Arnaud et al. |
| 2008/0305061 | A1* | 12/2008 | Bui ........................ A61K 8/891 424/63 |
| 2011/0104222 | A1 | 5/2011 | Iida et al. |

FOREIGN PATENT DOCUMENTS

| EP | 0 542 669 A1 | 5/1993 |
| EP | 0 787 730 A1 | 8/1997 |
| EP | 0 787 731 A2 | 8/1997 |
| EP | 0 847 752 A1 | 6/1998 |
| EP | 0 963 751 A2 | 12/1999 |
| EP | 0 963 757 A2 | 12/1999 |
| EP | 1 055 674 A1 | 11/2000 |
| EP | 1 847 247 A1 | 10/2007 |
| EP | 1 862 161 A1 | 12/2007 |
| EP | 1 862 162 A1 | 12/2007 |
| FR | 2 878 738 A1 | 6/2006 |
| JP | H11-001530 A | 1/1999 |
| JP | 2000-063225 A | 2/2000 |
| JP | 2009-57308 A | 3/2009 |
| WO | 96/08537 A1 | 3/1996 |
| WO | 03/045337 A2 | 6/2003 |
| WO | 2009/156375 A1 | 12/2009 |

OTHER PUBLICATIONS

Tonet et al., "Silicone Acrylate Copolymers in Mascara and Nail Varnish," Research Disclosure, Mason Publications, Hampshire, GB, vol. 505, No. 50, May 1, 2006.
"Silicone Acrylate Copolymers in Lipstick and Color Cosmetics," Research Disclosure, Jul. 2005, pp. 752-753.
International Search Report in International Application No. PCT/IB2009/053831I; dated Dec. 3, 2009.
Written Opinion of the International Searching Authority in International Application No. PCT/IB2009/053831; dated Dec. 3, 2009.
Extract of Cosmetic Encyclopedia (2003), p. 781-782, Japan (Partial English Translation Only).
Feb. 14, 2014, Office Action cited in Japanese Application No. 2011-525663 (with English Translation).
Jan. 10, 2018 Office Action Issued in U.S. Appl. No. 13/056,056.
Dec. 18, 2018 Office Action issued in U.S. Appl. No. 13/056,056.
The Kobo Silica Shells technical literature (Year: 2008).
Jul. 11, 2019 Office Action issued in U.S. Appl. No. 13/056,056.

* cited by examiner

*Primary Examiner* — Susan T Tran
(74) *Attorney, Agent, or Firm* — Oliff PLC

(57) ABSTRACT

A cosmetic composition for making up and/or caring for the skin, containing a physiologically acceptable medium containing at least one vinyl polymer having at least one carbosiloxane-dendrimer-derived unit and at least 2% by weight of a silica, relative to the total weight of the composition, the ratio by weight between said polymer and said silica being greater than or equal to 1.

12 Claims, No Drawings

COSMETIC COMPOSITION CONTAINING A POLYMER COMPRISING A CARBOSILOXANE DENDRIMER UNIT

This is a Continuation of application Ser. No. 13/056,056 filed Mar. 9, 2011, which is a National Stage Application of PCT/IB2009/053831 filed Sep. 2, 2009, and which claims the benefit of provisional application No. 61/098,806 filed Sep. 22, 2008. The entire disclosures of the prior applications are hereby incorporated by reference herein their entirety.

BACKGROUND

The present invention relates to the field of care and makeup for keratin materials, in particular the skin and the mucous membranes. More particularly, the present invention relates to compositions for conferring an effect of mattness and exhibiting an improved staying power over time of the mattness.

Cosmetic compositions, such as, for example, foundations, are commonly used to give the skin, in particular the face, color and an esthetic effect. These makeup products generally contain oils, pigments, fillers and, optionally, additives such as cosmetic or dermatological active agents.

It is known to those skilled in the art to use fillers to obtain a mattness effect. These fillers are most commonly selected according to their good properties of sebum absorption and/or to their ability to scatter light. However, their adhesion to the skin is generally weak, especially in the presence of sebum.

Film-forming polymers can then be used to improve the adhesion of these fillers, and to increase the staying power of the mattness effect over the course of the day.

These polymers are of very different chemical natures and can be carried in the fatty phase or in the aqueous phase. By way of examples of these polymers, mention may be made of silicone resins, polyacrylates, latices, etc.

Thus, U.S. Pat. No. 6,887,859 describes skin care and makeup compositions containing a combination of film-forming polymers and fillers.

While these formulations actually make it possible to confer certain mattness staying power properties on the cosmetic compositions, said properties may however be accompanied by unpleasant sensations and discomfort either during application of the product (difficult to spread, tacky effect, greasy feeling, etc.) or over the course of the day (tautness, mask effect, etc.).

FR 2 878 738 and EP 1 862 162 also describe cosmetic compositions containing a vinyl polymer comprising carbosiloxane-dendrimer-derived units and fillers.

However, there remains the need for cosmetic compositions exhibiting a mattness and an improved mattness staying power, which are pleasant and easy to apply, while at the same time conserving satisfactory application comfort, i.e. not having a feeling of tautness or a mask effect throughout the day and/or not inducing a greasy or tacky feeling when applied.

SUMMARY

The object of the present invention is to meet these needs.

The present disclosure relates to a cosmetic composition for making up and/or caring for the skin, comprising a physiologically acceptable medium, containing at least one vinyl polymer having at least one carbosiloxane-dendrimer-derived unit and at least 2% by weight of a silica relative to the total weight of the composition, the ratio by weight between said polymer and said silica being greater than or equal to 1.

Unexpectedly, the inventors have observed that the introduction, into a composition for making up and/or caring for the skin, of a vinyl polymer having at least one carbosiloxane-dendrimer-derived unit in combination with a silica makes it possible to confer very good mattness staying power properties on these compositions while at the same time maintaining satisfactory comfort on application. What is more, these compositions remain pleasant to wear throughout the day.

Up until now, it had never been shown that a combination of a polymer and of a silica, in accordance with the present disclosure, in a content and a weight ratio as required, made it possible to confer mattness and improved mattness staying power on cosmetic compositions while at the same time conferring, in a very satisfactory manner, comfortable feeling during application of the composition and during its use throughout the day.

As shown by the examples detailed hereafter, the specific selection of silica as filler, in an amount of at least 2%, and its combination with at least one carbosiloxane-dendrimer-derived unit in a weight ratio polymer/silica greater than or equal to 1 allow conferring to the compositions improved properties in terms of mattness and staying power of mattness.

WO 03/045337 and document RD 2005-495005 from Dow Corning, entitled "Silicone acrylate copolymers in lipstick and color cosmetic" describe, respectively, a mascara and an eye shadow containing a vinyl polymer comprising carbosiloxane-dendrimer-derived units and a silica.

Without wishing to be bound by any theory, the inventors have observed that, when the content of a vinyl polymer having at least one carbosiloxane-dendrimer-derived unit is less than that of the silica, the mattness staying power is not as good, and when the amount of polymer is too high compared with that of the silica, the cosmetic properties are degraded, in particular the comfort and sticking properties.

A subject of the present disclosure is also the use, in a cosmetic composition for making up and/or caring for the skin, of at least one vinyl polymer having at least one carbosiloxane-dendrimer-derived unit in combination with at least one silica in a ratio by weight of greater than or equal to 1, so as to confer on said composition an improved mattness staying power.

The present disclosure also relates to a nontherapeutic method for making up and/or caring for the skin, comprising at least the step of applying, to said skin, at least one layer of a composition according to the present disclosure.

DETAILED DESCRIPTION OF EMBODIMENTS

More particularly, the composition according to the present disclosure is different than a composition containing 21% by weight of cyclopentasiloxane, 4% by weight of propylsilsesquioxane wax substituted with alkyl units having at least 30 carbon atoms, 15% by weight of an acrylate/polytrimethylsiloxy methacrylate copolymer, 2% by weight of a cetyl PEG/PPG-10/1 dimethicone, 6% by weight of a dimethicone and dimethicone/polyglycerol-3 crosscopolymer, 3% by weight of silica, 1% by weight of nylon-12, 5% by weight of glycerol, 0.4% by weight of phenoxyethanol, 32.6% by weight of water and 10% by weight of a mixture of pigments formulated in cyclopentasiloxane.

According to embodiments, a composition comprises less than 4% by weight, relative to the total weight of the composition, of, or is more particularly free of, a propyl-silsesquioxane wax substituted with alkyl units having at least 30 carbon atoms.

According to embodiments, a composition may be contained in a container made from at least one nonthermoplastic material.

According to embodiments, a composition may be contained in a container made from at least one thermoplastic.

A cosmetic composition of the present disclosure may be in the form of a foundation, a hot-cast foundation product, a lipstick, a body makeup product, a concealer product or an eye shadow. It may be in the form of an anhydrous gel, in the form of a stick or a rod or in the form of a soft paste.

A composition of the present disclosure may comprise water or a hydrophilic phase, and may then in particular be in the form of an oil-in-water or water-in-oil emulsion or a W/O/W or O/W/O multiple emulsion, in particular when it is a foundation or a tinted cream.

A care composition according to the present disclosure may in particular be a suntan product or deodorant.

Mattness and Mattness Staying Power

The mattness and the mattness staying power can be measured by means of the protocol described below.

The mattness of a region of the skin, for example of the face, is measured using a polarimetric camera, which is a black and white polarimetric imaging system with which parallel (P) and crossed (C) polarized light images are acquired.

By analyzing the image resulting from the subtraction of the two images (P-C), shine is quantified by measuring the mean level of gray of the 5% of most shiny pixels corresponding to the regions of shine.

More specifically, the measurements are carried out on a panel of individuals, for example, a sample of 16 women, who are kept in an air-conditioned (22° C.+/−2° C.) waiting room for 15 min before the start of the test. They remove their makeup and an image of one of their cheeks is acquired with the polarimetric camera. This image makes it possible to measure the shine at T0 before applying makeup. Approximately 100 mg of cosmetic composition are then weighed out into a watchglass, and are applied, with the bare fingers, to the half of the face on which the measurement at T0 was carried out.

After a drying time of 15 min, an image of the made-up cheek is acquired with the polarimetric camera. This image makes it possible to measure the shine just after applying makeup (Timm). The models then return to the air-conditioned room for 3 h.

Finally, an image of the made-up cheek after 3 h of waiting is acquired with the polarimetric camera. This image makes it possible to measure the shine after 3 h of wearing makeup (T3h).

The results are expressed by calculating the difference (Timm−T0) which measures the effect of the makeup. A negative value signifies that the makeup reduces the shine of the skin and that it is therefore mattifying.

The difference (T3h−Timm) measuring the staying power of this effect is then calculated. The value obtained should be as low as possible, thereby signifying that the mattness of the makeup does not change over time.

Vinyl Polymer Grafted with a Carbosiloxane Dendrimer

A vinyl polymer suitable for the preparation of a composition according to the invention comprises at least one carbosiloxane-dendrimer-derived unit.

The vinyl polymer may have, in particular, a backbone and at least one side chain, which comprises a carbosiloxane-dendrimer-derived unit having a carbosiloxane dendrimer structure.

The term "carbosiloxane dendrimer structure" in the context of the present disclosure represents a molecular structure possessing branched groups having high molecular masses, said structure having a high regularity in the radial direction starting from the linkage to the backbone. Such carbosiloxane dendrimer structures are described in the form of a highly branched siloxane-silylalkylene copolymer in the Japanese patent application made available to public inspection Kokai 9-171 154.

A vinyl polymer may contain carbosiloxane-dendrimer-derived units which can be represented by the following general formula:

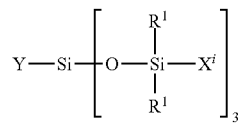

in which $R^1$ represents an aryl group or an alkyl group having from 1 to 10 carbon atoms, and $X^i$ represents a silylalkyl group which, when i=1, is represented by the formula:

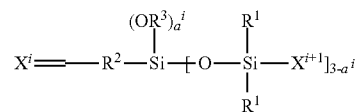

in which $R^1$ is as defined above, $R^2$ represents an alkylene group having from 2 to 10 carbon atoms, $R^3$ represents an alkyl group having from 1 to 10 carbon atoms, $X^{i+1}$ represents a hydrogen atom, an alkyl group having from 1 to 10 carbon atoms, an aryl group, or the silylalkyl group as defined above with i=i+1; i is an integer from 1 to 10 which represents the generation of said silylalkyl group, and $a^i$ is an integer from 0 to 3; Y represents a radical-polymerizable organic group selected from:

organic groups containing a methacrylic group or an acrylic group and which are represented by the formulae:

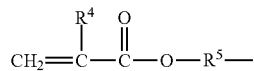

and

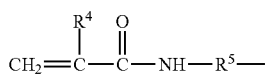

in which $R^4$ represents a hydrogen atom or an alkyl group, $R^5$ represents an alkylene group having from 1 to 10 carbon atoms, such as a methylene group, an ethylene group, a propylene group or a butylene group, the methylene group and the propylene group being preferred; and organic groups containing a styryl group and which are represented by the formula:

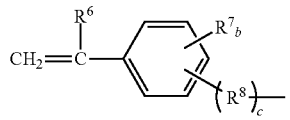

in which $R^6$ represents a hydrogen atom or an alkyl group, $R^7$ represents an alkyl group having from 1 to 10 carbon atoms, such as a methyl group, an ethyl group, a propyl group or a butyl group, the methyl group being preferred, $R^8$ represents an alkylene group having from 1 to 10 carbon atoms, such as a methylene group, an ethylene group, a propylene group or a butylene group, the ethylene group being preferred, b is an integer from 0 to 4, and c is 0 or 1 such that, if c is 0, —$(R^8)_c$— represents a bond.

According to embodiments, $R^1$ may represent an aryl group or an alkyl group having from 1 to 10 carbon atoms. The alkyl group may be represented by a methyl group, an ethyl group, a propyl group, a butyl group, a pentyl group, an isopropyl group, an isobutyl group, a cyclopentyl group or a cyclohexyl group, such as a methyl group. The aryl group may be represented by a phenyl group and a naphthyl group, such as a phenyl group.

A vinyl polymer having at least one carbosiloxane-dendrimer-derived unit has a molecular side chain containing a carbosiloxane dendrimer structure, and can be derived from the polymerization:

(A) of 0 to 99.9 parts by weight of a vinyl monomer; and
(B) of 100 to 0.1 parts by weight of a carbosiloxane dendrimer containing a radical-polymerizable organic group, represented by the general formula:

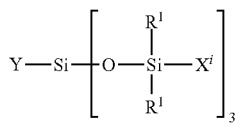

in which Y represents a radical-polymerizable organic group, $R^1$ represents an aryl group or an alkyl group having from 1 to 10 carbon atoms, and $X^i$ represents a silylalkyl group which, when i=1, is represented by the formula:

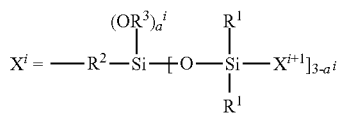

in which $R^1$ is as defined above, $R^2$ represents an alkylene group having from 2 to 10 carbon atoms, $R^3$ represents an alkyl group having from 1 to 10 carbon atoms, $X^{i+1}$ represents a hydrogen atom, an alkyl group having from 1 to 10 carbon atoms, an aryl group, or the silylalkyl group as defined above with i=i+1; i is an integer from 1 to 10 which represents the generation of said silylalkyl, and $a^i$ is an integer from 0 to 3;

where said radical-polymerizable organic group contained in the component (B) is selected from:
  organic groups containing a methacrylic group or an acrylic group and which are represented by the formulae:

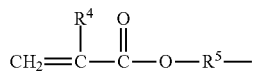

and

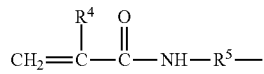

in which $R^4$ represents a hydrogen atom or an alkyl group, $R^5$ represents an alkylene group having from 1 to 10 carbon atoms; and
  organic groups containing a styryl group and which are represented by the formula:

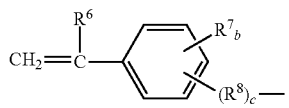

in which $R^6$ represents a hydrogen atom or an alkyl group, $R^7$ represents an alkyl group having from 1 to 10 carbon atoms, $R^8$ represents an alkylene group having from 1 to 10 carbon atoms, b is an integer from 0 to 4, and c is 0 or 1, such that, if c is 0, —$(R^8)_c$-represents a bond.

The monomer of vinyl type that is the component (A) in the vinyl polymer is a monomer of vinyl type which contains a radical-polymerizable vinyl group.

There is no particular limitation as regards such a monomer.

The following are examples of this vinyl-type monomer: methyl methacrylate, ethyl methacrylate, n-propyl methacrylate, isopropyl methacrylate, or a methacrylate of a lower alkyl analog; glycidyl methacrylate; butyl methacrylate, butyl acrylate, n-butyl methacrylate, isobutyl methacrylate, tert-butyl acrylate, tert-butyl methacrylate, n-hexyl methacrylate, cyclohexyl methacrylate, 2-ethylhexyl acrylate, 2-ethylhexyl methacrylate, octyl methacrylate, lauryl methacrylate, stearyl acrylate, stearyl methacrylate, or a higher-analog methacrylate; vinyl acetate, vinyl propionate, or a vinyl ester of a lower fatty acid analog; vinyl caproate, vinyl 2-ethylhexoate, vinyl laurate, vinyl stearate, or an ester of a higher fatty acid analog; styrene, vinyltoluene, benzyl methacrylate, phenoxyethyl methacrylate, vinylpyrrolidone, or similar vinyl aromatic monomers; methacrylamide, N-methylolmethacrylamide, N-methoxy-methylmethacrylamide, isobutoxymethoxymethacrylamide, N,N-dimethylmethacrylamide, or similar monomers of vinyl type containing amide groups; hydroxyethyl methacrylate, hydroxypropyl methacrylate, or similar monomers of vinyl type containing hydroxyl groups; acrylic acid, methacrylic acid, itaconic acid, crotonic acid, fumaric acid, maleic acid, or similar monomers of vinyl type containing a carboxylic acid group; tetrahydrofurfuryl methacrylate, butoxyethyl methacrylate, ethoxydiethylene glycol methacrylate, polyethylene glycol methacrylate, polypropylene glycol monomethacrylate, hydroxybutyl vinyl ether, cetyl vinyl ether, 2-ethylhexyl vinyl ether, or a similar monomer of vinyl type with ether bonds; metharyloxypropyltrimethoxysilane, polydimethylsiloxane containing a methacrylic group on one of its molecular ends, polydimethylsiloxane containing a styryl group on one of its molecular ends, or a similar silicone compound containing unsaturated groups; butadiene; vinyl chloride; vinylidene chloride; methacrylonitrile; dibutyl fumarate; anhydrous maleic acid; anhydrous succinic acid; methacryl glycidyl ether; an organic salt of an amine, an ammonium salt, and an alkali metal salt of methacrylic acid, of itaconic acid, of crotonic acid, of maleic acid or of fumaric acid; a radical-polymerizable unsaturated monomer containing a sulfonic acid group such as a styrenesulfonic acid group; a quaternary ammonium salt derived from methacrylic acid, such as 2-hydroxy-3-methacryloxypropyltrimethylammonium chloride; and a methacrylic acid ester of an alcohol containing a tertiary amine group, such as a methacrylic acid ester of diethylamine.

Multifunctional monomers of vinyl type may also be used.

The following represent examples of such compounds: trimethylolpropane trimethacrylate, pentaerythritol trimethacrylate, ethylene glycol dimethacrylate, tetraethylene glycol dimethacrylate, polyethylene glycol dimethacrylate, 1,4-butanediol dimethacrylate, 1,6-hexanediol dimethacrylate, neopentyl glycol dimethacrylate, trimethylolpropanetrioxyethyl methacrylate, tris(2-hydroxyethyl)isocyanurate dimethacrylate, tris(2-hydroxyethyl)isocyanurate trimethacrylate, polydimethylsiloxane capped with styryl groups containing divinylbenzene groups on both ends, or similar silicone compounds containing unsaturated groups.

A carbosiloxane dendrimer, which is the component (B), can be represented by the following formula:

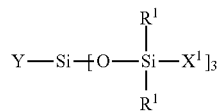

in which Y represents a radical-polymerizable organic group as defined above.

The following represent suitable examples of a radical-polymerizable organic group Y: an acryloxymethyl group, a 3-acryloxypropyl group, a methacryloxymethyl group, a 3-methacryloxypropyl group, a 4-vinylphenyl group, a 3-vinylphenyl group, a 4-(2-propenyl)phenyl group, a 3-(2-propenyl)phenyl group, a 2-(4-vinylphenyl)ethyl group, a 2-(3-vinylphenyl)ethyl group, a vinyl group, an allyl group, a methallyl group and a 5-hexenyl group.

$R^1$ is as defined above.

$X^i$ represents a silylalkyl group which is represented by the following formula, when i is equal to one:

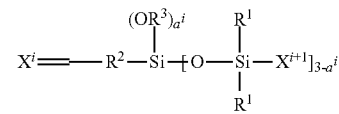

in which $R^1$ is as defined above.

$R^2$ represents an alkylene group having from 2 to 10 carbon atoms, such as an ethylene group, a propylene group, a butylene group, a hexylene group, or a similar linear alkylene group; a methylmethylene group, a methylethylene group, a 1-methylpentylene group, a 1,4-dimethylbutylene group, or a similar branched alkylene group, such as ethylene, methylethylene, hexylene, l-methylpentylene and 1,4-dimethylbutylene groups. $R^3$ represents an alkyl group having from 1 to 10 carbon atoms, such as methyl, ethyl, propyl, butyl and isopropyl groups.

$X^{i+1}$ represents a hydrogen atom, an alkyl group having from 1 to 10 carbon atoms, an aryl group, or the silylalkyl group with i=i+1.

$a^i$ is an integer from 0 to 3, and i is an integer from 1 to 10 which indicates the generation number, which represents the number of repetitions of the silylalkyl group.

For example, when the generation number is equal to one, the carbosiloxane dendrimer may be represented by the first general formula shown below, in which Y, $R^1$, $R^2$ and $R^3$ are as defined above, $R^{12}$ represents a hydrogen atom or is identical to $R^1$; $a^1$ is identical to $a^i$. In embodiments, the mean total number of $OR^3$ groups in a molecule is within the range from 0 to 7.

When the generation number is equal to 2, the carbosiloxane dendrimer may be represented by the second general formula shown below, in which Y, $R^1$, $R^2$, $R^3$ and $R^{12}$ are the same as defined above; $a^1$ and $a^2$ represent the $a^i$ of the indicated generation. Preferably, the mean total number of $OR^3$ groups in a molecule is in the range from 0 to 25.

When the generation number is equal to 3, the carbosiloxane dendrimer is represented by the third general formula shown below, in which Y, $R^1$, $R^2$, $R^3$ and $R^{12}$ are the same as defined above; $a^1$, $a^2$ and $a^3$ represent the a of the indicated generation. In embodiments, the mean total number of $OR^3$ groups in a molecule is in the range from 0 to 79.

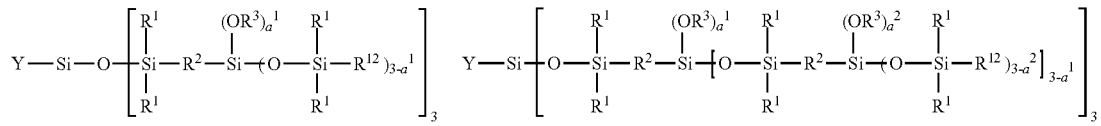

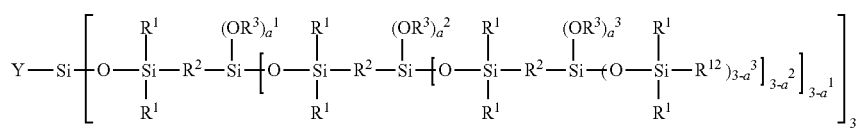

Carbosiloxane dendrimers that contain a radical-polymerizable organic group may be represented by the following mean structural formulae:
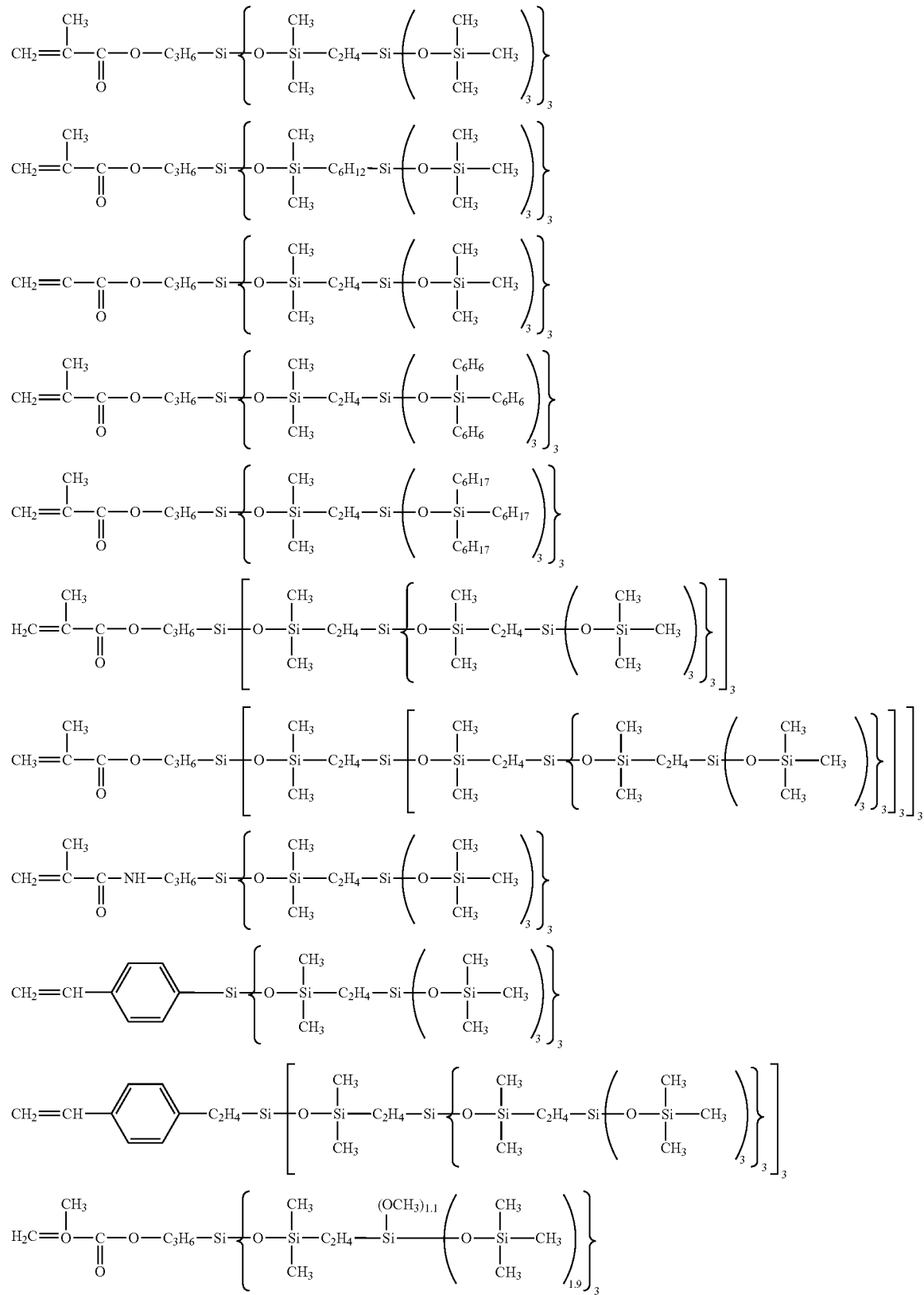

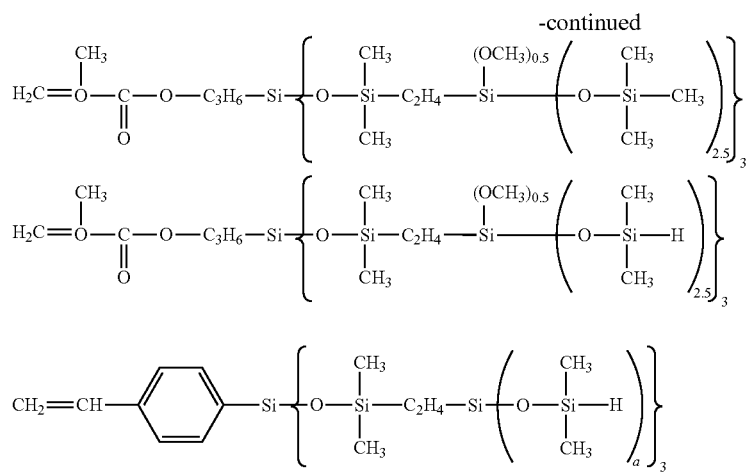

The carbosiloxane dendrimer may be produced according to the process for producing a branched silalkylene siloxane described in Japanese patent application Hei 9-171 154.

For example, it may be prepared by subjecting an organosilicon compound containing a hydrogen atom linked to a silicon atom, represented by the following general formula:

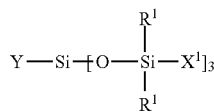

and an organosilicon compound containing an alkenyl group, to a hydrosilylation reaction.

In the above formula, the organosilicon compound may be represented by 3-methacryloxypropyltris(dimethylsiloxy)silane, 3-acryloxypropyltris- may be selected from polymers such that the carbosiloxane-dendrimer-derived unit is (dimethylsiloxy)silane, and 4-vinylphenyltris(dimethylsiloxy)silane. The organosilicon compound that contains an alkenyl group may be represented by vinyltris(trimethylsiloxy)silane, vinyltris(dimethylphenylsiloxy)silane, and 5-hexenyltris(trimethylsiloxy)silane.

The hydrosilylation reaction is carried out in the presence of a chloroplatinic acid, a complex of vinylsiloxane and of platinum, or a similar transition metal catalyst.

A vinyl polymer having at least one carbosiloxane-dendrimer-derived unit may be selected from polymers such that the unit of a derivative of a carbosiloxane dendrimer is a carbosiloxane dendrimer structure represented by formula (I):

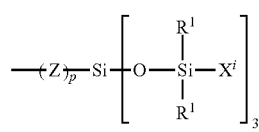

in which Z is a divalent organic group, "p" is 0 or 1, $R^1$ is an aryl or alkyl group having from 1 to 10 carbon atoms and $X^i$ is a silylalkyl group represented by formula (II):

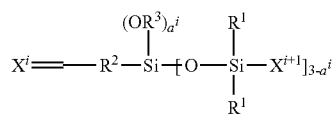

in which $R^1$ is as defined above, $R^2$ is an alkylene group having from 1 to 10 carbon atoms, $R^3$ is an alkyl group having from 1 to 10 carbon atoms, and $X^{i+1}$ is a group selected from the group comprising hydrogen atoms, aryl groups and alkyl groups having up to 10 carbon atoms, and silylalkyl groups $X^i$ where the "i" is an integer from 1 to 10 indicating the generation of the silylalkyl group beginning in each carbosiloxane dendritic structure with a value of 1 for the $X^i$ group in formula (I) and the index "a'" is an integer from 0 to 3.

In a vinyl polymer having at least one carbosiloxane-dendrimer-derived unit, the polymerization ratio between the components (A) and (B), in terms of the weight ratio between (A) and (B), may be within a range from 0/100 to 99.9/0.1, or even from 0.1/99.9 to 99.9/0.1, and preferably within a range from 1/99 to 99/1. A ratio between the components (A) and (B) of 0/100 means that the compound becomes a homopolymer of component (B).

A vinyl polymer having at least one carbosiloxane-dendrimer-derived unit may be obtained by copolymerization of the components (A) and (B), or by polymerization of the component (B) alone.

The polymerization may be a free-radical polymerization or an ionic polymerization.

The polymerization may be carried out by bringing about a reaction between the components (A) and (B) in a solution for a period of from 3 to 20 hours in the presence of a radical initiator at a temperature of from 50° C. to 150° C.

A suitable solvent for this purpose is hexane, octane, decane, cyclohexane or a similar aliphatic hydrocarbon; benzene, toluene, xylene or a similar aromatic hydrocarbon; diethyl ether, dibutyl ether, tetrahydrofuran, dioxane, or similar ethers; acetone, methyl ethyl ketone, methyl isobutyl ketone, diisobutyl ketone, or similar ketones; methyl acetate, ethyl acetate, butyl acetate, isobutyl acetate or similar esters; methanol, ethanol, isopropanol, butanol or similar alcohols; octamethylcyclotetrasiloxane, decamethylcyclopentasiloxane, hexamethyldisiloxane, octamethyltrisiloxane or a similar organosiloxane oligomer.

A radical initiator may be any compound known in the art for standard free-radical polymerization reactions. The specific examples of such radical initiators are 2,2'-azobis (isobutyronitrile), 2,2'-azobis(2-methylbutyronitrile), 2,2'-azobis(2,4-dimethylvaleronitrile) or similar compounds of azobis type; benzoyl peroxide, lauroyl peroxide, tert-butyl peroxybenzoate, tert-butyl peroxy-2-ethylhexanoate or a similar organic peroxide. These radical initiators may be used alone or in a combination of two or more. The radical initiators may be used in an amount of from 0.1 to 5 parts by weight per 100 parts by weight of the components (A) and (B). A chain-transfer agent may be added. The chain-transfer agent may be 2-mercaptoethanol, butyl mercaptan, n-dodecyl mercaptan, 3-mercaptopropyltrimethoxysilane, a polydimethylsiloxane containing a mercaptopropyl group, or a similar compound of mercapto type; methylene chloride, chloroform, carbon tetrachloride, butyl bromide, 3-chloropropyltrimethoxysilane or a similar halogenated compound.

In the production of the polymer of vinyl type, after polymerization, the residual unreacted vinyl monomer may be removed under conditions of heating under vacuum.

To facilitate the preparation of the mixture of the starting material of cosmetic products, the number-average molecular mass of the vinyl polymer containing a carbosiloxane dendrimer may be selected within the range of between 3000 and 2,000,000, such as between 5000 and 800,000. It may be a liquid, a gum, a paste, a solid, a powder or any other form. In embodiments, other forms include solutions constituted of the dilution, in solvents, of a dispersion or of a powder.

The vinyl polymer may be a dispersion of a polymer of vinyl type having a carbosiloxane dendrimer structure in its side molecular chain, in a liquid such as a silicone oil, an organic oil, an alcohol or water.

The silicone oil may be a dimethylpolysiloxane with the two molecular ends capped with trimethylsiloxy groups, a copolymer of methylphenylsiloxane and of dimethylsiloxane having the two molecular ends capped with trimethylsiloxy groups, a copolymer of methyl-3,3,3-trifluoropropylsiloxane and of dimethylsiloxane having the two molecular ends capped with trimethylsiloxy groups, or similar unreactive linear silicone oils, and also hexamethylcyclotrisiloxane, octamethylcyclotetrasiloxane, decamethylcyclo-pentasiloxane, dodecamethylcyclohexasiloxane, or a similar cyclic compound. In addition to the unreactive silicone oils, modified polysiloxanes containing functional groups such as silanol groups, amino groups and polyether groups on the ends or within the side molecular chains may be used.

The organic oils may be isododecane, liquid paraffin, isoparaffin, hexyl laurate, isopropyl myristate, myristyl myristate, cetyl myristate, 2-octyldodecyl myristate; isopropyl palmitate, 2-ethylhexyl palmitate, butyl stearate, decyl oleate, 2-octyldodecyl oleate, myristyl lactate, cetyl lactate, lanolin acetate, stearyl alcohol, cetostearyl alcohol, oleyl alcohol, avocado oil, almond oil, olive oil, cocoa oil, jojoba oil, gum oil, sunflower oil, soybean oil, camelia oil, squalane, castor oil, cotton seed oil, coconut oil, egg yolk oil, propylene glycol monooleate, neopentyl glycol 2-ethylhexanoate, or a similar glycol ester oil; triglyceryl isostearate, the triglyceride of a fatty acid of coconut oil, or a similar oil of a polyhydric alcohol ester; polyoxyethylene lauryl ether, polyoxypropylene cetyl ether or a similar polyoxyalkylene ether.

The alcohol may be of any type that is suitable for use in combination with a cosmetic product starting material. For example, it may be methanol, ethanol, butanol, isopropanol or similar lower alcohols.

A solution or a dispersion of the alcohol should have a viscosity in the range from 10 to $10^9$ mPa at 25° C. To improve the sensory use properties in a cosmetic product, the viscosity may be within the range from 100 to $5 \times 10^8$ mPa·s.

The solutions and the dispersions may be readily prepared by mixing a vinyl polymer having at least one carbosiloxane-dendrimer-derived unit with a silicone oil, and organic oil, an alcohol or water. The liquids may be present in the step of polymerization of a vinyl polymer having at least one carbosiloxane-dendrimer-derived unit. In this case, the unreacted residual vinyl monomer should be completely removed by heat treatment of the solution or dispersion under atmospheric pressure or reduced pressure.

In the case of a dispersion, the dispersity of the polymer of vinyl type may be improved by adding a surfactant.

Such a surfactant may be hexylbenzenesulfonic acid, octylbenzenesulfonic acid, decylbenzenesulfonic acid, dodecylbenzenesulfonic acid, cetylbenzenesulfonic acid, myristylbenzenesulfonic acid or anionic surfactants such as sodium salts of these acids; octyltrimethylammonium hydroxide, dodecyltrimethylammonium hydroxide, hexadecyltrimethylammonium hydroxide, octyldimethylbenzylammonium hydroxide, decyldimethylbenzylammonium hydroxide, dioctadecyldimethylammonium hydroxide, tallow-trimethylammonium hydroxide, coconut oil-trimethylammonium hydroxide, or a similar cationic surfactant; a polyoxyalkylene alkyl ether, a polyoxyalkylenealkylphenol, a polyoxyalkylene alkyl ester, the sorbitol ester of polyoxyalkylene, polyethylene glycol, polypropylene glycol, an ethylene oxide additive of diethylene glycol trimethylnonanol, and nonionic surfactants of polyester type, and also mixtures.

In addition, the solvents and the dispersions may be combined with iron oxide suitable for use with cosmetic products, or a similar pigment, and also zinc oxide, titanium oxide, silicon oxide, mica, talc or similar inorganic oxides in powder form. In the dispersion, a mean particle diameter of the polymer of vinyl type may be within a range of between 0.001 and 100 microns, such as between 0.01 and 50 microns. This is because, outside the recommended range, a cosmetic product mixed with the emulsion will not have a nice enough feel on the skin or to the touch, or sufficient spreading properties or a pleasant feel.

A vinyl polymer contained in the dispersion or the solution may have a concentration in a range of between 0.1% and 95% by weight, such as between 5% and 85% by weight. However, to facilitate the handling and the preparation of the mixture, the range may be between 10% and 75% by weight.

A vinyl polymer suitable for the present disclosure may also be one of the polymers described in the examples of application EP 0 963 751.

According to embodiments, a vinyl polymer grafted with a carbosiloxane dendrimer may be derived from the polymerization:

(A) of 0.1 to 99 part(s) by weight of one or more acrylate or methacrylate monomer(s); and (B) of 100 to 0.1 part(s) by weight of an acrylate or methacrylate monomer of a tri[tri(trimethylsiloxy)silylethyldimethylsiloxy]silylpropyl carbosiloxane dendrimer.

According to embodiments, a vinyl polymer having at least one carbosiloxane-dendrimer-derived unit may comprise a unit derived from a tri[tri(trimethylsiloxy)silylethyldimethylsiloxy]silylpropyl carbosiloxane dendrimer corresponding to one of the formulae:

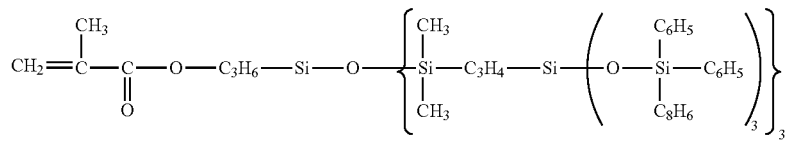

or

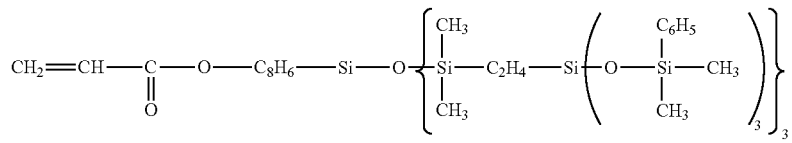

According to embodiments, a vinyl polymer having at least one carbosiloxane-dendrimer-derived unit, used in the present disclosure, comprises at least one butyl acrylate monomer.

According to embodiments, a vinyl polymer may also comprise at least one organofluorine group.

Structures in which the polymerized vinyl units constitute the backbone and carbosiloxane dendritic structures and also organofluorine groups are attached to side chains are particularly preferred.

The organofluorine groups may be obtained by replacing with fluorine atoms all or some of the hydrogen atoms of methyl, ethyl, propyl, isopropyl, butyl, isobutyl, tert-butyl, pentyl, neopentyl, hexyl, cyclohexyl, heptyl, octyl, nonyl, decyl, undecyl, dodecyl, tridecyl, tetradecyl, hexadecyl and octadecyl groups and other alkyl groups having from 1 to 20 carbon atoms, and also alkyloxyalkylene groups having from 6 to 22 carbon atoms.

The groups represented by the formula: —$(CH_2)_x$—$(CF_2)_y$—$R^{13}$ are suggested by way of examples of fluoroalkyl groups obtained by substituting fluorine atoms for hydrogen atoms of alkyl groups. In the formula, the index "x" is 0, 1, 2 or 3 and "y" is an integer from 1 to 20. $R^1$ is an atom or a group selected from a hydrogen atom, a fluorine atom, —$(CH(CF_3)_2$— or $CF(CF_3)_2$. Such fluorine-substituted alkyl groups are exemplified by linear or branched polyfluoroalkyl or perfluoroalkyl groups represented by the formulae given below:
—$CF_3$, —$C_2F_5$, -n$C3F7$, —$CF(CF_3)_2$, -n$C_4F_9$, $CF_2CF(CF_3)_2$, -n$C_5F_{11}$, -n$C_6F_3$, -n$C_8F_{17}$, $CH_2CF_3$, —$(CH(CF_3)_2$, $CH_2CH(CF_3)_2$—$CH_2(CF_2)_2F$, —$CH_2(CF_2)_3F$, —$CH_2(CF_2)_4F$, $CH_2(CF_2)_6F$, $CH_2(CF_2)_6F$, —$CH_2CH_2CF_3$, —$CH_2CH_2(CF_2)_2F$, —$CH_2CH_2(CF_2)_3F$, —$CH_2CH_2(CF_2)_4F$, —$CH_2CH_2(CF_2)_6F$, —$CH_2CH_2(CF_2)_8F$, —$CH_2CH_2(CF_2)_{10}F$, —$CH_2CH_2(CF_2)_{12}F$, $CH_2CH_2(CF_2)_{14}F$, —$CH_2CH_2(CF_2)_{16}F$, —$CH_2CH_2CH_2CF_3$, —$CH_2CH_2CH_2(CF_2)_2F$, —$CH_2CH_2CH_2(CF_2)_2H$—$CH_2(CF_2)_4H$, and —$CH_2CH_2(CF_2)_3H$.

The groups represented by —$CH_{2c}H_2$—$(CF_2)_m$—$CFR^{14}$—$[OCF_2CF(CF_3)]_n$—$OC_3F_7$ are suggested as fluoroalkyloxyfluoroalkylene groups obtained by substituting fluorine atoms for hydrogen atoms of alkyloxyalkylene groups. In the formula, the index "m" is 0 or 1, "n" is 0, 1, 2, 3, 4 or 5, and $R^{14}$ is a fluorine atom or $CF_3$. Such fluoroalkyloxyfluoroalkylene groups are exemplified by the perfluoroalkyloxyfluoro-alkylene groups represented by the formulae given below:

—$CH_2CH_2CF(CF_3)$—$[OCF_2CF(CF_3)]_n$—$OC_3F_7$,
—$CH_2CH_2CF_2CF_2$—$[OCF_2CF(CF_3)]n$-$OC_3F_7$.

The number-average molecular weight of the vinyl polymer used in the present disclosure may be between 3000 and 2,000,000, such as between 5000 and 800,000.

This type of fluorinated vinyl polymer may be obtained by addition:

of a vinyl monomer (B) not containing any organofluorine groups in the molecule, to a vinyl monomer containing organofluorine groups in the molecule (A), and a carbosiloxane dendrimer (C) containing radical-polymerizable organic groups represented by general formula (III):

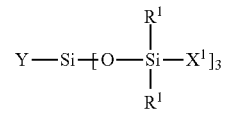

in which Y is a radical-polymerizable organic group and $R^1$ and $X^i$ are as defined above, and by subjecting them to a copolymerization.

Thus, according to embodiments, a composition may comprise a vinyl polymer having at least one carbosiloxane-dendrimer-derived unit and which is derived from the copolymerization:

(A) of vinyl monomers containing organofluorine groups in the molecule, (B) optionally of vinyl monomers not containing any organofluorine groups in the molecule, and (C) of carbosiloxane dendrimers having radical-polymerizable organic groups represented by general formula (III):

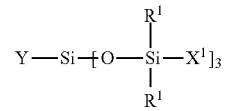

in which Y is a radical-polymerizable organic group, $R^1$ is an aryl or alkyl group having from 1 to 10 carbon atoms and X is a silylalkyl group represented by formula (II) below:

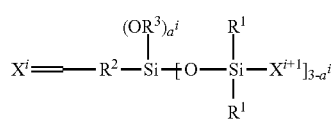

in which $R^1$ is as above, $R^2$ is an alkylene group having from 1 to 10 carbon atoms, $R^3$ is an alkyl group having from 1 to 10 carbon atoms, and $X^{i+1}$ is a group selected from the group comprising hydrogen atoms, aryl groups and alkyl groups having up to 10 carbon atoms, and silylalkyl groups $X^i$ mentioned above where the "i" is an integer from 1 to 10 indicating the generation of said silylalkyl group beginning in each carbosiloxane dendritic structure with a value of 1 for the group $X^i$ in formula (III), and the index "a'" is an integer from 0 to 3, said vinyl polymer having a copolymerization ratio of the component (A) to the component (B) of 0.1 to 100:99.9 to 0% by weight, and a copolymerization ratio of the sum of the component (A) and of the component (B) to the component (C) of 0.1 to 99.9:99.9 to 0.1% by weight.

The vinyl monomers (A) containing organofluorine groups in the molecule may be monomers represented by the general formula:

$$(CH^2)=CR^{15}COOR^f.$$

In the formula, $R^{15}$ is a hydrogen atom or a methyl group, $R^f$ is an organofluorine group exemplified by the fluoroalkyl and fluoroalkyloxyfluoroalkylene groups described above. The compounds represented by the formulae given below are suggested by way of specific examples of the component (A). In the formulae given below, "z" is an integer from 1 to 4.

$CH_2$=$CCH_3COO$—$CF_3$, $CH_2$=$CCH_3COO$—$C_2F_5$, $CH_2$=$CCH3COO$-$nC_3F_7$, $CH_2$=$CCH_3COO$—$CF(CF_3)_2$, $CH_2$=$CCH_3COO$-$nC_4F_9$, $CH_2$=$CCH_3COO$—$CF(CF_3)_2$, $CH_2$=$CCH_3COO$-$nC_5F_{11}$, $CH_2$=$CCH_3COO$-$nC_6F_{13}$, $CH_2$=$CCH_3COO$-$nC_8F_{17}$, $CH_2$=$CCH_3COO$—$CH_2CF_3$, $CH_2$=$CCH_3COO$—$CH(CF_3)_2$, $CH_2$=$CCH_3COO$—$CH_2CH(CF_3)_2$, $CH_2$=$CCH_3COO$—$CH_2(CF_2)_2F$, $CH_2$=$CCH_3COO$—$CH_2(CF_2)_2F$, $CH_2$=$CCH_3COO$—$CH_2(CF_2)_4F$, $CH_2$=$CCH_3COO$—$CH_2(CF_2)_6F$, $CH_2$=$CCH_3COO$—$CH_2(CF_2)_8F$, $CH_2$=$CCH_3COO$—$CH_2CH_2CF_3$, $CH_2$=$CCH_3COO$—$CH_2CH_2(CF_2)_2F$, $CH_2$=$CCH_3COO$—$CH_2CH_2(CF_2)_3F$, $CH_2$=$CCH_3COO$—$CH_2CH_2(CF_2)_4F$, $CH_2$=$CCH_3COO$—$CH_2CH_2(CF_2)_6F$, $CH_2$=$CCH_3COO$—$CH_2CH_2(CF_2)_8F$, $CH_2$=$CCH_3COO$—$CH_2CH_2(CF_2)_{10}F$, $CH_2$=$CCH_3COO$—$CH_2CH_2(CF_2)_{12}F$, $CH_2$=$CCH_3COO$—$CH_2CH_2(CF_2)_{14}F$, $CH_2$=$CCH_3COO$—$CH_2$—$CH_2$—$(CF_2)_{16}F$, $CH_2$=$CCH_3COO$—$CH_2CH_2CH_2CF_3$, $CH_2$=$CCH_3COO$—$CH_2CH_2CH_2(CF_2)_2F$, $CH_2$=$CCH_3COO$—$CH_2CH_2CH_2(CF_2)_2H$, $CH_2$=$CCH_3COO$—$CH_2(CF_2)_4H$, $CH_2$=$CCH_3COO$—$(CF_2)_3H$, $CH_2$=$CCH_3COO$—$CH_2CH_2CF(CF_3)$—[$OCF_2$—$CF(CF_3)$]z-$OC_3$ $F_7$, $CH_2$=$CCH_3COO$—$CH_2CH_2CF_2CF_2$—[$OCF_2$—$CF(CF_3)$]z-$OC_3$ $F_7$, $CH_2$=$CHCOO$—$CF_3$, $CH2$=$CHCOO$—$C_2F_5$, $CH_2$=$CHCOO$-$nC_3F_7$, $CH_2$=$CHCOO$—$CF(CF_3)_2$, $CH_2$=$CHCOO$-$nC_4F_9$, $CH_2$=$CHCOO$—$CF_2CF(CF_3)_2$, $CH_2$=$CHCOO$-$nCSF_{11}$, $CH_2$=$CHCOO$-$nC_6F_{13}$, $CH_2$=$CHCOO$-$nC_8F_{17}$, $CH_2$=$CHCOO$—$CH_2CF_3$, $CH_2$=$CHCOO$—$CH(CF_3)$, $CH_2$=$CHCOO$—$CH_2CH(CF_3)_2$, $CH_2$=$CHCOO$—$CH_2(CF_2)_2F$, $CH_2$=$CHCOO$—$CH_2(CF_2)_3F$, $CH_2$=$CHCOO$—$CH_2(CF_2)_4F$, $CH_2$=$CHCOO$—$CH_2(CF_2)_6F$, $CH_2$=$CHCOO$—$CH_2(CF_2)_8F$, $CH_2$=$CHCOO$—$CH_2CH_2CF_3$, $CH_2$=$CHCOO$—$CH_2CH_2(CF_2)_2F$, $CH_2$=$CHCOO$—$CH_2CH_2(CF_2)_3F$, $CH_2$=$CHCOO$—$CH_2CH_2(CF_2)_4F$, $CH_2$=$CHCOO$—$CH_2CH_2(CF_2)_6F$, $CH_2$=$CHCOO$—$CH_2CH_2(CF_2)_8F$, $CH_2$=$HCOO$—$CH_2CH_2(CF_2)_{10}F$, $CH_2$=$CHCOO$—$CH_2CH_2$—$(CF_2)_{12}F$, $CH_2$=$CHCOO$—$CH_2CH_2(CF_2)_{14}F$, $CH_2$=$CHCOO$—$CH_2CH_2(CF_2)_{16}F$, $CH_2$=$CHCOO$—$CH_2CH_2CH_2CF_3$, $CH_2$=$CHCOO$—$CH_2CH_2CH_2(CF_2)_2F$, $CH_2$=$CHCOO$—$CH_2CH_2CH_2$ $(CF_2)_2H$, $CH_2$=$CHCOO$—$CH_2(CF_2)_4H$, $CH_2$=$CHCOO$—$CH_2CH_2(CF_2)_3H$, $CH_2$=$CHCOO$—$CH_2CH_2CF(CF_3)$— [$OCF_2$—$CF(CF_3)$]z-$OC_3$ $F_7$, $CH_2$=$CHCOO$—$CH_2CH_2CF_2CF_2(CF_3)$—[$OCF_2$—$CF (CF_3)$]$_2$—$OC_3$ $F_7$, such as $CH_2$=$CHCOO$—$CH_2CH_2 (CF_2)_6F$, $CH_2$=$CHCOO$—$CH_2CH_2(CF_2)_8F$, $CH_2$=$CCH_3 COO$—$CH_2CH_2(CF_2)_6F$, $CH_2$=$CCH_3COO$—$CH_2CH_2 (CF_2)_8F$, $CH_2$=$CHCOO$—$CH_2CF_3$, $CH_2$=$CCH_3COO$—$CH_2CF_3$, or such as $CH_2$=$CHCOO$—$CH_2CF_3$, $CH_2$=$CCHCOO$—$CH_2CF_3$.

The vinyl monomers (B) not containing any organofluorine groups in the molecule may be any monomers containing radical-polymerizable vinyl groups which are exemplified, for example, by methyl acrylate, methyl methacrylate, ethyl acrylate, ethyl methacrylate, n-propyl acrylate, n-propyl methacrylate, isopropyl acrylate, isopropyl methacrylate, and other lower alkyl acrylates or methacrylates; glycidyl acrylate, glycidyl methacrylate; n-butyl acrylate, n-butyl methacrylate, isobutyl acrylate, isobutyl methacrylate, tert-butyl acrylate, tert-butyl methacrylate, n-hexyl acrylate, n-hexyl methacrylate, n-hexyl acrylate, n-hexyl methacrylate, cyclohexyl acrylate, cyclohexyl methacrylate, 2-ethylhexyl acrylate, 2-ethylhexyl methacrylate, octyl acrylate, octyl methacrylate, lauryl acrylate, lauryl methacrylate, stearyl acrylate, stearyl methacrylate, and other higher acrylates and methacrylates; vinyl acetate, vinyl propionate, and other lower fatty acid vinyl esters; vinyl butyrate, vinyl caproate, vinyl 2-ethylhexanoate, vinyl laurate, vinyl stearate, and other higher fatty acid esters; styrene, vinyltoluene, benzyl acrylate, benzyl methacrylate, phenoxyethyl acrylate, phenoxyethyl methacrylate, vinylpyrrolidone, and other vinylaromatic monomers; dimethylaminoethyl acrylate, dimethylaminoethyl methacrylate, diethylaminoethyl acrylate, diethylaminoethyl methacrylate, and other aminovinyl monomers, acrylamide, methacrylamide, N-methylolacrylamide, N-methylolmethacrylamide, N-methoxymethylacrylamide, N-methoxymethylmethacrylamide, isobutoxymethoxyacrylamide, isobutoxymethoxy-methacrylamide, N,N-dimethylacrylamide, N,N-dimethylmethacrylamide, and other vinylamide monomers; hydroxyethyl acrylate, hydroxyethyl methacrylate, acrylic acid hydroxypropyl alcohol, methacrylic acid hydroxypropyl alcohol, and other hydroxy vinyl monomers; acrylic acid, methacrylic acid, itaconic acid, crotonic acid, fumaric acid, maleic acid, and other vinylcarboxylic acid monomers; tetrahydrofurfuryl acrylic, tetrahydrofurfuryl methacrylate, butoxyethyl acrylate, butoxyethyl methacrylate, ethoxydiethylene glycol acrylate, ethoxydiethylene glycol methacrylate, polyethylene glycol acrylate, polyethylene glycol methacrylate, polypropylene glycol monoacrylate, polypropylene glycol monomethacrylate, hydroxybutyl vinyl ether, cetyl vinyl ether, 2-ethylhexyl vinyl ether and other vinyl monomers containing an ether bond; acryloxypropyltrimethoxysilane, methacryloxypropyltrimethoxysilane, polydimethyl-siloxanes containing acryl or methacryl groups at one of the ends, polydimethylsiloxanes containing alkenylaryl groups at one of the ends and other silicone compounds containing unsaturated groups; butadiene; vinyl chloride; vinylidene chloride, acrylonitrile, methacrylonitrile; dibutyl fumarate; maleic anhydride; dodecylsuccinic anhydride; acryl glycidyl ether, methacryl glycidyl ether, 3,4-epoxycyclohexylmethyl acrylate, 3,4-epoxy-cyclohexylmethyl methacrylate, alkali metal salts, ammonium salts and organic amine salts of acrylic acid, of methacrylic acid, of itaconic acid, of crotonic acid, of fumaric acid, of maleic acid and of other radical-polymerizable unsaturated carboxylic acids, radical-polymerizable unsaturated monomers containing sulfonic acid groups, such as styrene sulfonic acid and also the alkali metal salts thereof, the ammonium salts thereof and the organic amine salts thereof; the quaternary ammonium salts derived from acrylic acid or from methacrylic acid, such as 2-hydroxy-3-methacryloxypropyltrimethylammonium chloride, methacrylic acid esters of a tertiary amine alcohol, such as the diethylamine ester of methacrylic acid and quaternary ammonium salts thereof.

In addition, it is also possible to use, by way of vinyl monomers (B), the polyfunctional vinyl monomers which are exemplified, for example, by trimethylolpropane triacrylate, trimethylolpropane trimethacrylate, pentaerythritol triacrylate, pentaerythritol trimethacrylate, ethylene glycol diacrylate, ethylene glycol dimethacrylate, tetraethylene glycol diacrylate, tetraethylene glycol dimethacrylate, polyethylene glycol diacrylate, polyethylene glycol dimethacrylate, 1,4-butanediol diacrylate, 1,4-butanediol dimethacrylate, 1,6-hexanediol diacrylate, 1,6-hexanediol dimethacrylate, neopentyl glycol diacrylate, neopentyl glycol dimethacrylate, trimethylolpropanetrioxyethyl acrylate, trimethylolpropanetrioxyethyl methacrylate, tris(2-hydroxyethyl)isocyanurate diacrylate, tris(2-hydroxyethyl)isocyanurate dimethacrylate, tris(2-hydroxyethyl)isocyanurate triacrylate, tris(2-hydroxyethyl)isocyanurate trimethacrylate, polydimethylsiloxane in which the two ends of the molecular chain are blocked with alkenylaryl groups, and other silicone compounds containing unsaturated groups.

As regards the ratio mentioned above in which the component (A) and the component (B) are copolymerized, the weight ratio of the compound (A) to the compound (B) should be within the range from 0.1:99.9 to 100:0, such as within the range 1:99 to 100:0.

The carbosiloxane dendrimer (C) is represented by general formula (III) indicated above.

In the component (C), Y may be a radical-polymerizable organic group, the type of which is not subject to any special limitations provided that it is an organic group capable of undergoing a radical addition reaction.

Y may be selected, for example, from organic groups containing acrylic or methacrylic groups, organic groups containing an alkenylaryl group, or alkenyl groups having from 2 to 10 carbon atoms.

The organic groups containing acrylic or methacrylic groups may be represented by the general formulae:

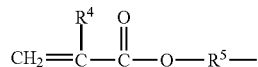

and

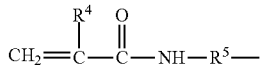

The alkenylaryl group may be represented by the formula:

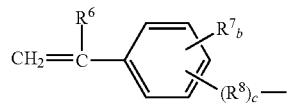

In the formulae above, $R^4$ and $R^6$ are hydrogen atoms or methyl groups, $R^5$ and $R^8$ are alkylene groups having from 1 to 10 carbon atoms, and $R^7$ is an alkyl group having from 1 to 10 carbon atoms. The index "b" is an integer from 0 to 4, and "c" is 0 or 1.

Acryloxymethyl, 3-acryloxypropyl, methacryloxymethyl, 3-methacryloxypropyl, 4-vinylphenyl, 3-vinylphenyl, 4-(2-propenyl)phenyl, 3-(2-propenyl)phenyl, 2-(4-vinylphenyl) ethyl, 2-(3-vinylphenyl)enyl, vinyl, allyl, methallyl and 5-hexenyl are suggested by way of examples of such radical-polymerizable organic groups.

The "i" in formula (II), which is an integer from 1 to 10, is the number of generations of said silylalkyl group, in other words the number of times that the silylalkyl group is repeated.

Thus, the carbosiloxane dendrimer of this component with a generation number of 1 is represented by the general formula:

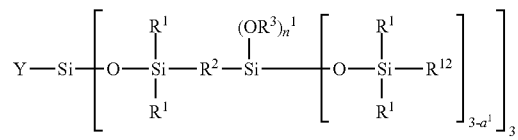

in which Y, $R^1$, $R^2$ and $R^3$ are as above and $R^{12}$ is a hydrogen atom or as $R^1$ described above. The index "$a^1$" is an integer from 0 to 3, the average total of "$a^1$" per molecule being from 0 to 7.

The carbosiloxane dendrimers of this component with a generation number of 2 are represented by the general formula:

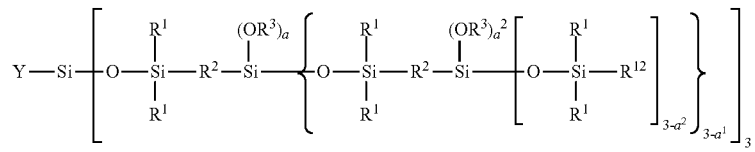

in which Y, $R^1$, $R^2$, $R^3$ and $R^{12}$ are as above and the indices "$a^1$" and "$a^2$" are integers from 0 to 3, the average total of "$a^1$" and "$a^2$" per molecule being from 0 to 25.

The carbosiloxane dendrimers of this component with a generation number of 3 are represented by the general formula:

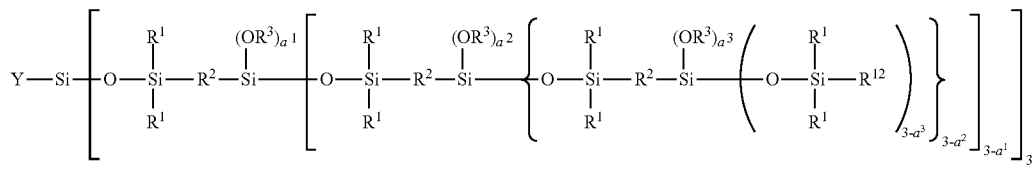

in which Y, $R^1$, $R^2$, $R^3$ and $R^{12}$ are as above and the indices "$a^1$", "$a^2$" and "$a^3$" are integers from 0 to 3, the average total of "$a^1$", of "$a^2$" and of "$a^3$" per molecule being from 0 to 79.

The component (C) can be exemplified by carbosiloxane dendrimers represented by formulae of mean composition, represented below:

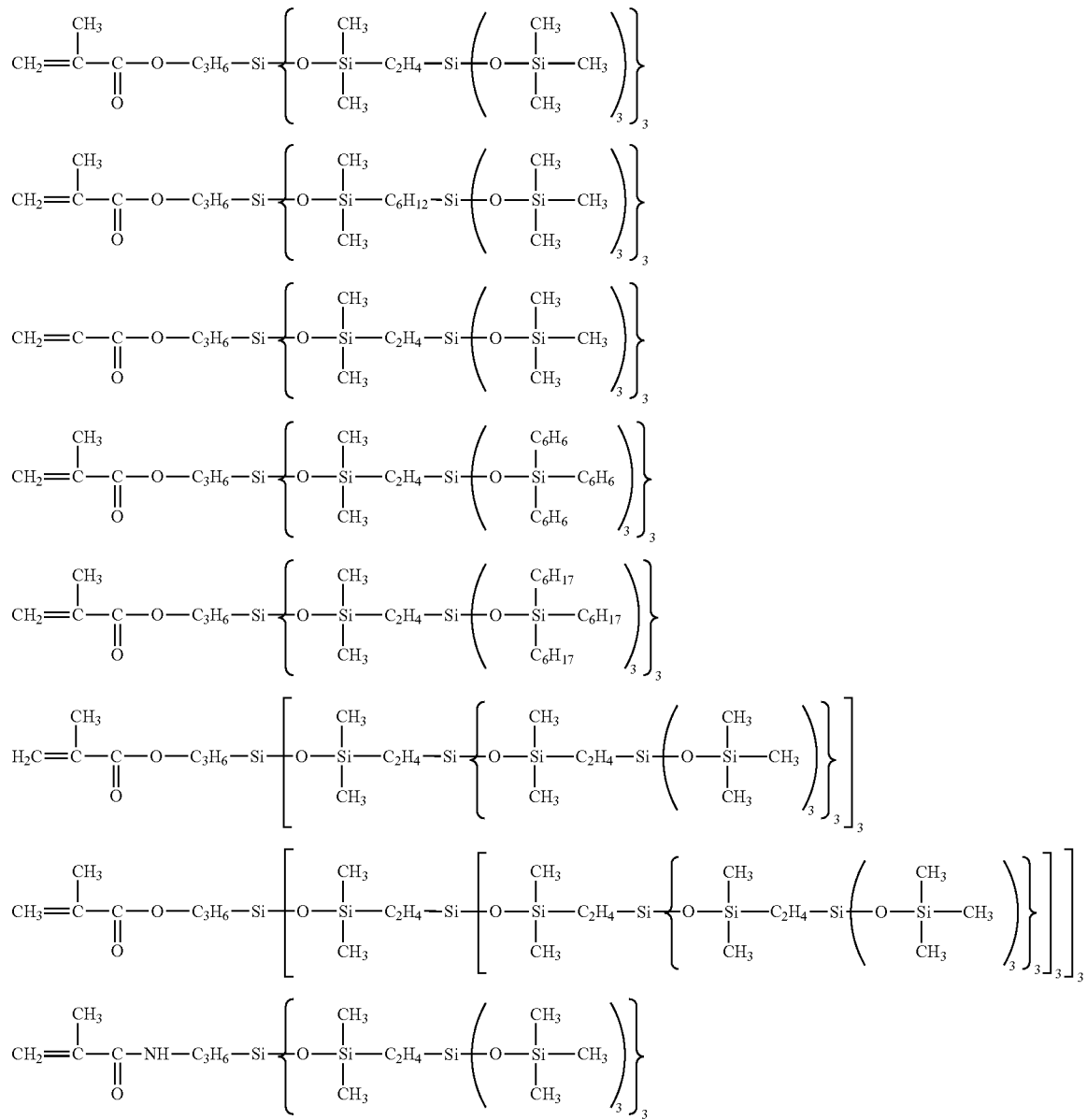

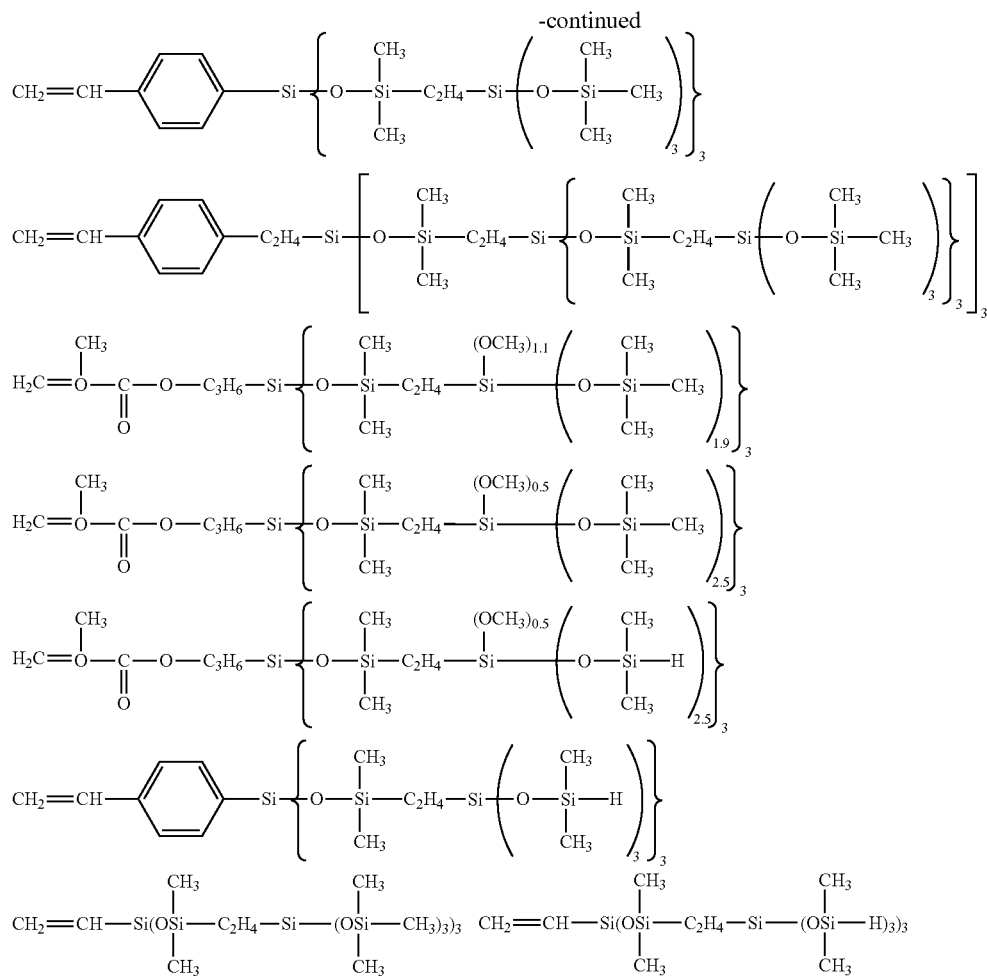

In embodiments, the carbosiloxane-dendrimer-derived unit comprises at least one tri[tri(trimethylsiloxy)silylethyldimethylsiloxy]silylpropyl carbosiloxane-dendrimer-derived unit corresponding to one of the formulae:

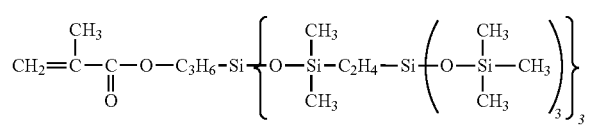

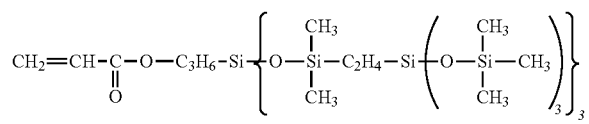

The carbosiloxane dendrimers of the component (C) may be prepared using the process for preparing the siloxane/silylalkylene branched copolymers described in document EP 1 055 674.

For example, they may be prepared by subjecting organic alkenyl silicone compounds and silicone compounds comprising hydrogen atoms linked to the silicon, represented by the general formula:

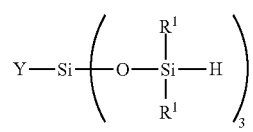

in which $R^1$ and Y are as defined above, to a hydrosilylation reaction.

For example, 3-methacryloxypropyltris(dimethylsiloxy)silane, 3-acryloxypropyltris(dimethylsiloxy)silane and 4-vinylphenyltris(dimethylsiloxy)silane are used as silicon compounds represented by the above formula. Vinyltris(trimethyl-siloxy)silane, vinyltris(dimethylphenylsiloxy)silane and 5-hexenyltris(trimethylsiloxy)-silane are used as organosilicon alkenyl compounds. In addition, it is preferable to perform the hydrosilylation reaction in the presence of a transition metal catalyst such as chloroplatinic acid and the platinum/vinylsiloxane complex.

The copolymerization ratio of the component (C), in terms of its weight ratio relative to the total weight of compound (A) and of compound (B), may be within the range from 0.1:99.9 to 99.9:0.1, such as within the range 1:99 to 99:1, or within the range from 5:95 to 95:5.

Amino groups may be introduced into the side chains of the vinyl polymer using, included in the component (B), vinyl monomers containing amino groups, such as dimethylaminoethyl acrylate, dimethylaminoethyl methacrylate, diethylaminoethyl acrylate and diethylaminoethyl methacrylate, followed by performing a modification with potassium acetate monochloride, ammonium acetate monochloride, the aminomethylpropanol salt of monochloroacetic acid, the triethanolamine salt of monobromoacetic acid, sodium monochloropropionate, and other alkali metal salts of halogenated fatty acids; otherwise, carboxylic acid groups may be introduced into the side chains of the vinyl polymer using, included in the component (B), vinyl monomers containing carboxylic acids, such as acrylic acid, methacrylic acid, itaconic acid, crotonic acid, fumaric acid and maleic acid, and the like, followed by neutralizing the product with triethylamine, diethylamine, triethanolamine and other amines.

A fluorinated vinyl polymer may be one of the polymers described in the examples of application WO 03/045337.

According to embodiments, a grafted vinyl polymer for the purpose of the present disclosure may be carried in an oil or a mixture of oil(s), such as volatile oil(s), in particular selected from silicone oils and hydrocarbon-based oils and mixtures thereof.

According to embodiments, a suitable silicone oil may be cyclopentasiloxane.

According to embodiments, a suitable hydrocarbon-based oil may be isododecane.

The vinyl polymers grafted with at least one carbosiloxane-dendrimer-derived unit that may be particularly suitable for the present disclosure are the polymers sold under the names TIB 4-100, TIB 4-101, TIB 4-120, TIB 4-130, TIB 4-200, FA 4002 ID (TIB 4-202), TIB 4-220 and FA 4001 CM (TIB 4-230) by the company Dow Corning.

A composition of the present disclosure may comprise a vinyl polymer having at least one carbosiloxane-dendrimer-derived unit in a content with respect to active material ranging from 2% to 20% by weight, relative to the total weight of the composition, such as ranging from 3% to 15% by weight, ranging from 4% to 13% by weight, or ranging from 5% to 12% by weight of active material of vinyl polymer having at least one carbosiloxane-dendrimer-derived unit, relative to the total weight of the composition.

Silica

A composition comprises at least one silica introduced in particulate form.

A silica suitable for the present disclosure is a hydrophilic or hydrophobic silica selected from precipitated silicas, fumed silicas and mixtures thereof.

A silica suitable for the present disclosure may be spherical or nonspherical in shape, and porous or nonporous.

In embodiments, a silica suitable for the present disclosure is spherical and porous.

The porosity of a silica particle may be opened to the exterior or in the form of a central cavity.

A silica suitable for the present disclosure may be in the form of particles of nanometric or micrometric mean size.

In particular, a silica suitable for the present disclosure may be in the form of particles having a mean size ranging from 5 nm to 25 µm, such as from 20 nm to 20 microns, or from 1000 nm (or 1 µm) to 10 µm.

A silica may be hydrophilic or hydrophobic in nature. In the latter case, the surface of the silicas is chemically modified by chemical reaction in order to create a decrease in the number of silanol groups.

A composition of the present disclosure may advantageously comprise a hydrophobic silica.

The silica particles may be treated with hexamethyldisilazane so as to obtain trimethylsiloxyl groups, or with dimethyldichlorosilane or alternatively with a polydimethylsiloxane.

As examples of commercial references of silica suitable for the present disclosure, mention may be made of the silicas sold under the references Silica Beads SB 150 and SB 700 from Miyoshi, having a mean size of 5 microns, and the Sunspheres H33, H51 and H53 from Asahi glass, having respective sizes of 3, 5 and 5 microns.

A composition according to the present disclosure may comprise particles of fumed silica.

The particles of fumed silica suitable for implementation of the present disclosure may be hydrophilic or be surface-treated so as to be rendered hydrophobic.

The hydrophilic fumed silicas may be obtained by high-temperature hydrolysis of a volatile silicon compound in an oxhydric flame, producing a finely divided silica. The hydrophilic silicas may have a large number of silanol groups at their surface.

Such hydrophilic silicas are, for example, sold under the names "AEROSIL 90®", "AEROSIL 130®", "AEROSIL 1 150®", "AEROSIL 200®", "AEROSIL 255®", "AEROSIL 300®", and "AEROSIL 380®" by the company Degussa, and "CAB-O-SIL HS-5®", "CAB-O-SIL EH-5®", "CAB-O-SIL LM-130®", "CAB-O-SIL MS-55®", and "CAB-O-SIL M-5®" by the company Cabot.

The hydrophobic fumed silicas can be obtained by modification of the surface of the silica by means of a chemical reaction that creates a decrease in the number of silanol groups, it being possible for these groups to be in particular substituted with hydrophobic groups.

The hydrophobic groups may be:

trimethylsiloxyl groups, which are in particular obtained by treatment of fumed silica in the presence of hexamethyldisilazane. Silicas treated in this way are called "Silica silylate" according to the CTFA (6th edition, 1995). They are, for example, sold under the references "AEROSIL R202®", "AEROSIL R805®" and "AEROSIL R812®" by the company Degussa, and "CAB-O-SIL TS-530®" by the company Cabot, dimethylsilyloxyl or polydimethylsiloxane groups, which are in particular obtained by treatment of fumed silica in the presence of polydimethylsiloxane or of dimethyldichlorosilane. Silicas treated in this way are called "Silica dimethyl silylate" according to the CTFA (6th edition, 1995). They are, for example, sold under the references "AEROSIL R972®" and "AEROSIL R974®" by the company Degussa, and "CAB-O-SIL TS-610®" and "CAB-O-SIL TS-720®" by the company Cabot.

According to embodiments, the silica may be carried in the fatty phase.

A composition of the present disclosure may comprise from 2% to 15% by weight of silica relative to the total weight of the composition, such as from 3% to 10%, or from 3.5% to 7% by weight of silica, relative to the total weight of the composition.

According to embodiments, a composition may comprise at least one vinyl polymer having at least one carbosiloxane-dendrimer-derived unit and at least one silica in a weight ratio of greater than or equal to 1 and less than or equal to 10, such as greater than or equal to 1 and less than or equal to 8, ranging from 1.5 to 5, or ranging from 1.5 to 3.

Physiologically Acceptable Medium

In addition to the compounds indicated above, a composition according to the present disclosure comprises a physiologically acceptable medium.

The term "physiologically acceptable medium" is intended to denote a medium that is particularly suitable for the application of a composition of the present disclosure to the skin or the lips.

The physiologically acceptable medium is generally suitable for the nature of the support to which the composition should be applied, and also for the way in which the composition should be conditioned.

A composition of the present disclosure may be a dispersion or an emulsion.

A dispersion may be prepared in an aqueous phase or in an oily phase.

An emulsion may have an oily or aqueous continuous phase. Such an emulsion may, for example, be an invert emulsion (W/O) or a direct emulsion (O/W), or else a multiple emulsion (W/O/W or O/W/O).

Aqueous Phase

The composition may comprise an aqueous phase.

The aqueous phase comprises water. A water suitable for the present disclosure may be a floral water such as cornflower water and/or a mineral water such as Vittel water, Lucas water or La Roche Posay water and/or a spring water.

The aqueous phase may also comprise organic solvents that are water-miscible (at ambient temperature–25° C.) for instance monoalcohols having from 2 to 6 carbon atoms, such as ethanol or isopropanol; polyols having in particular from 2 to 20 carbon atoms, such as from 2 to 10 carbon atoms, or having from 2 to 6 carbon atoms, such as glycerol, propylene glycol, butylene glycol, pentylene glycol, hexylene glycol, dipropylene glycol or diethylene glycol; glycol ethers (having in particular from 3 to 16 carbon atoms), such as mono-, di- or tripropylene glycol ($C_1$-$C_4$)alkyl ethers, mono-, di- or triethylene glycol ($C_1$-$C_4$)alkyl ethers, and mixtures thereof.

The aqueous phase may also comprise stabilizers, for example sodium chloride, magnesium chloride and magnesium sulfate.

The aqueous phase may also comprise any water-soluble or water-dispersible compound compatible with an aqueous phase, such as gelling agents, film-forming polymers, thickeners, surfactants and mixtures thereof.

In particular, a composition may comprise an aqueous phase in a content ranging from 1% to 80% by weight, such as from 5% to 50%, or from 10% to 45% by weight, relative to the total weight of the composition.

According to embodiments, a composition of the present disclosure may be anhydrous.

An anhydrous composition may comprise less than 5% by weight of water, relative to the total weight of the composition, such as less than 3%, less than 2%, or less than 1% by weight of water, relative to the total weight of the composition.

More particularly, an anhydrous composition may be free of water.

Fatty Phase

A cosmetic composition in accordance with the present disclosure may comprise at least one liquid and/or solid fatty phase.

In particular, a composition of the present disclosure may comprise at least one liquid fatty phase, in particular at least one oil as mentioned hereinafter.

The term "oil" is intended to mean any fatty substance in liquid form at ambient temperature (20-25° C.) and at atmospheric pressure.

A composition may comprise a liquid fatty phase in a content ranging from 1% to 90%, such as from 5% to 80%, from 10% to 70%, or from 20% to 50% by weight, relative to the total weight of the composition.

The oily phase suitable for the preparation of the cosmetic compositions according to the present disclosure may comprise hydrocarbon-based, silicone, fluoro or non-fluoro oils, or mixtures thereof.

The oils may be volatile or non-volatile.

They may be of animal, plant, mineral or synthetic origin.

For the purpose of the present disclosure, the term "volatile oil" is intended to mean an oil (or nonaqueous medium) capable of evaporating on contact with the skin in less than one hour, at ambient temperature and at atmospheric pressure. The volatile oil is a volatile cosmetic oil which is liquid at ambient temperature, having in particular a non-zero vapor pressure, at ambient temperature and at atmospheric pressure, in particular having a vapor pressure ranging from 0.13 Pa to 40,000 Pa (10- to 300 mmHg), and preferably ranging from 1.3 Pa to 13,000 Pa (0.01 to 100 mmHg), and preferentially ranging from 1.3 Pa to 1300 Pa (0.01 to 10 mmHg).

For the purpose of the present disclosure, the term "non-volatile oil" is intended to mean an oil having a vapor pressure of less than 0.13 Pa.

For the purpose of the present disclosure, the term "silicone oil" is intended to mean an oil comprising at least one silicon atom, and in particular at least one SiO group.

The term "fluoro oil" is intended to mean an oil comprising at least one fluorine atom.

The term "hydrocarbo-based oil" is intended to mean an oil containing mainly hydrogen and carbon atoms.

The oils may optionally comprise oxygen, nitrogen, sulfur and/or phosphorus atoms, for example in the form of hydroxyl or acid radicals.

Volatile Oils

The volatile oils may be selected from hydrocarbon-based oils having from 8 to 16 carbon atoms, and in particular branched $C_8$-$C_{16}$ alkanes (also known as isoparaffins), such as isododecane (also known as 2,2,4,4,6-pentamethylheptane), isodecane or isohexadecane, and, for example, the oils sold under the trade names ISOPARS® or PERMETH-YLS®.

Use may also be made, as volatile oils, of volatile silicones, such as, for example, volatile linear or cyclic silicone oils, in particular those having a viscosity ≤8 centistokes (cSt) ($8 \times 10^{-6}$ $m^2$/s) and having in particular from 2 to 10 silicon atoms, and in particular from 2 to 7 silicon atoms, these silicon atoms optionally comprising alkyl or alkoxy groups having from 1 to 10 carbon atoms. As volatile silicone oil that can be used in the present disclosure, mention may in particular be made of dimethicones having a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltdtrasiloxane, dodecamethylpentasiloxane, and mixtures thereof.

Use may also be made of volatile fluoro oils, such as nonafluoromethoxybutane or perfluoromethylcyclopentane, and mixtures thereof.

According to embodiments, a composition may comprise from 1% to 80% by weight, or even from 5% to 70% by weight, or even from 10% to 60% by weight, and in particular from 15% to 50% by weight of volatile oil, relative to the total weight of the composition.

Non-Volatile Oils

The non-volatile oils may in particular be selected from non-volatile hydrocarbon-based, fluoro and/or silicone oils.

As non-volatile hydrocarbon-based oil, mention may in particular be made of:

hydrocarbon-based oils of animal origin, such as perhydrosqualene, hydrocarbon-based oils of plant origin, such as phytostearyl esters, for instance phytostearyl oleate, phytostearyl isostearate and lauroyl/octyldodecyl/phytostearyl glutamate (Ajinomoto, Eldew PS203), triglycerides constituted of fatty acid esters of glycerol, in particular in which the fatty acids may have chain lengths ranging from $C_4$ to $C_{36}$, and in particular from $C_{18}$ to $C_{36}$, it being possible for these oils to be linear or branched, and saturated or unsaturated; these oils may in particular be heptanoic or octanoic triglycerides, shea oil, alfalfa oil, poppy seed oil, pumpkin oil, millet oil, barley oil, quinoa oil, rye oil, candlenut oil, passionflower oil, shea butter, aloe oil, sweet almond oil, peach kernel oil, groundnut oil, argan oil, avocado oil, baobab oil, borrage oil, broccoli oil, calendula oil, camelina oil, canola oil, carrot oil, safflower oil, hemp oil, rapeseed oil, cotton seed oil, coconut oil, marrow seed oil, wheatgerm oil, jojoba oil, lilly oil, macadamia oil, corn oil, meadowfoam oil, St. John's Wort oil, monoi oil, hazelnut oil, apricot kernel oil, nut oil, olive oil, evening primrose oil, palm oil, blackcurrent seed oil, kiwi seed oil, grapeseed oil, pistachio oil, pumpkin oil, winter squash oil, quinoa oil, musk rose oil, sesame oil, soya oil, sunflower oil, castor oil and watermelon oil, and mixtures thereof, or alternatively caprylic/capric acid triglycerides, for instance those sold by the company Stéarineries Dubois or those sold under the names MIGLYOL 810®, 812® and 818® by the company Dynamit Nobel;

linear or branched hydrocarbons of mineral or synthetic origin, such as liquid paraffins and derivatives thereof, petroleum jelly, polydecenes, polybutenes, hydrogenated polyisobutene such as Parleam, squalane;

synthetic ethers having from 10 to 40 carbon atoms;

synthetic esters, for instance oils of formula $R_1COOR_2$, in which $R_1$ represents a linear or branched fatty acid residue containing from 1 to 40 carbon atoms, and $R_2$ represents a hydrocarbon-based chain, in particular a branched chain, containing from 1 to 40 carbon atoms provided that $R_1+R_2$ is $\geq 10$. The esters may in particular be selected from fatty acid and alcohol esters, for instance: cetostearyl octanoate, isopropyl alcohol esters, such as isopropyl myristate, isopropyl palmitate, ethyl palmitate, 2-ethylhexyl palmitate, isopropyl stearate or isostearate, isostearyl isostearate, octyl stearate, hydroxylated esters, for instance isostearyl lactacte, octyl hydroxystearate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate and palmitate, alkyl benzoate, polyethylene glycol diheptanoate, propylene glycol 2-diethylhexanoate, and mixtures thereof, $C_{12}$-$C_{15}$ alkyl benzoates, hexyl laurate, neopentanoic acid esters, for instance isodecyl neopentanoate, isotridecyl neopentanoate, isostearyl neopentanoate, or octyldodecyl neopentanoate, isononanoic acid esters, for instance isononyl isononanoate, isotridecyl isononanoate and octyl isononanoate, hydroxylated esters such as isostearyl lactate and diisostearyl malate;

polyol esters and pentaerythritol esters, for instance dipentaerythrityl tetrahydroxystearate/tetraisostearate, esters of diol dimers and diacid dimers, such as LUSPLAN DD-DA5® and LUSPLAN DD-DA7®, sold by the company Nippon Fine Chemical and described in application US 2004-175338, copolymers of a diol dimer and of a diacid dimer and esters thereof, such as copolymers of dilinoleyl diol dimers/dilinoleic dimers and esters thereof, for instance Plandool-G, copolymers of polyols and of diacid dimers, and esters thereof, such as Hailuscent ISDA, or the copolymer of dilinoleic acid/butanediol, fatty alcohols that are liquid at ambient temperature, with a branched and/or unsaturated carbon chain having from 12 to 26 carbon atoms, for instance 2-octyldodecanol, isostearyl alcohol, oleyl alcohol, 2-hexyldecanol, 2-butyloctanol and 2-undecylpentadecanol, $C_{12}$-$C_{22}$ higher fatty acids, such as oleic acid, linoleic acid or linolenic acid, and mixtures thereof, and dialkyl carbonates, the two alkyl chains possibly being identical or different, such as the dicaprylyl carbonate sold under the name CETIOL CC® by Cognis, oils of higher molar mass having in particular a molar mass ranging from approximately 400 to approximately 10,000 g/mol, in particular from approximately 650 to approximately 10,000 g/mol, in particular from approximately 750 to approximately 7500 g/mol, and more particularly ranging from approximately 1000 to approximately 5000 g/mol. As oils of higher molar mass that can be used in the present disclosure, mention may in particular be made of the oils selected from:

lipophilic polymers, linear fatty acid esters having a total carbon number ranging from 35 to 70, hydroxylated esters, aromatic esters, esters of $C_{24}$-$C_{28}$ branched fatty acids or fatty alcohols, silicone oils, oils of plant origin, and mixtures thereof;

fluoro oils optionally partially hydrocarbon-based and/or silicone-based, such as fluorosilicone oils, fluorinated polyethers or fluorinated silicones, as described in document EP-A-847 752;

silicone oils, such as polydimethylsiloxanes (PDMS) which are non-volatile and linear or cyclic; polydimethylsiloxanes comprising alkyl, alkoxy or phenyl groups which are pendant or at the end of the silicone chain, said groups having from 2 to 24 carbon atoms; phenylated silicones, such as phenyl trimethicones, phenyl dimethicones, phenyltrimethylsiloxydiphenylsiloxanes, diphenyl dimethicones, diphenylmethyldiphenyl-trisiloxanes or (2-phenylethyl) trimethylsiloxysilicates, and mixtures thereof.

According to embodiments, the fatty phase of the composition may contain only volatile compounds.

Lipophilic Structuring Agent

A composition according to the present disclosure may comprise at least one agent for structuring a liquid fatty phase, selected from a wax, a pasty compound, and mixtures thereof.

In particular, a wax suitable for the present disclosure may especially be selected from waxes of animal, plant, mineral and synthetic origin, and mixtures thereof.

By way of examples of waxes that can be used according to the present disclosure, mention may be made of:

waxes of animal origin, such as beeswax, spermaceti, lanolin wax and lanolin derivatives, plant waxes such as camauba wax, candelilla wax, ouricury wax, Japan wax, cocoa butter, cork fiber wax or sugarcane wax, mineral waxes, for example paraffin wax, petroleum jelly wax, lignite wax or microcrystalline waxes or ozokerites, synthetic waxes, among which are polyethylene waxes, and waxes obtained by Fisher-Tropsch synthesis, silicone waxes, in particular substituted linear polysiloxanes; mention may, for example, be made of silicone polyether waxes, alkyl dimethicones or alkoxy dimethicones having from 16 to 45 carbon atoms, alkyl methicones such as the $C_{30}$-$C_{45}$ alkyl methicone sold under the trade name "AMS C 30®" by Dow Corning, hydrogenated oils that are solid at 25° C., such as hydrogenated castor oil, hydrogenated jojoba oil, hydrogenated palm oil, hydrogenated tallow or hydrogenated coconut oil, and fatty esters that are solid at 25° C., for instance the $C_{20}$-$C_{40}$ alkyl stearate sold under the trade name "KESTER WAX K82H®" by the company Koster Keunen, and/or mixtures thereof.

In embodiments, polyethylene waxes, microcrystalline waxes, carnauba waxes, hydrogenated jojoba oil, candelilla waxes, beeswaxes and/or mixtures thereof may be used.

A composition may comprise at least one pasty compound.

The presence of a pasty compound may make it possible to advantageously confer improved comfort when a composition of the present disclosure is deposited on keratin fibers.

Such a compound may be advantageously selected from lanolin and derivatives thereof; polymeric or nonpolymeric silicone compounds; polymeric or nonpolymeric fluoro compounds; vinyl polymers, in particular olefin homopolymers; olefin copolymers; hydrogenated diene homopolymers and copolymers; linear or branched and homo- or copolymeric oligomers of alkyl (meth)acrylates preferably having a $C_8$-$C_{30}$ alkyl group; homo- and copolymeric oligomers of vinyl esters having $C_8$-$C_{30}$ alkyl groups; homo- and copolymeric oligomers of vinyl ethers having $C_8$-$C_{30}$ alkyl groups; liposoluble polyethers resulting from polyetherification between one or more $C_2$-$C_{100}$, in particular $C_2$-$C_{50}$ diols; fatty acid or alcohol esters; and mixtures thereof.

Among the esters, mention may in particular be made of:

the esters of an oligomeric glycerol, especially the esters of diglycerol, for instance polyglyceryl-2 triisostearate, the condensates of adipic acid and of glycerol, for which a portion of the hydroxyl groups of the glycerols have reacted with a mixture of fatty acids, such as stearic acid, capric acid, stearic acid and isostearic acid and 12-hydroxystearic acid, such as in particular those sold under the trade mark Softisan 649 by the company Sasol, or such as bisdiglyceryl polyacyladipate-2; the arachidyl propionate sold under the trade mark Waxenol 801 by Alzo; phytosterol esters; triglycerides of fatty acids and derivatives thereof, such as hydrogenated cocoglycerides; noncrosslinked polyesters resulting from polycondensation between a linear or branched $C_4$-$C_{50}$ dicarboxylic acid or polycarboxylic acid and a $C_2$-$C_{50}$ diol or polyol; aliphatic esters of an ester resulting from the esterification of an aliphatic hydroxycarboxylic acid ester with an aliphatic carboxylic acid; polyesters resulting from the esterification, with a polycarboxylic acid, of an aliphatic hydroxycarboxylic acid ester, said ester comprising at least two hydroxyl groups, such as the products RISOCAST DA-H® and RISOCAST DA-L®; and mixtures thereof.

The structuring agent(s) may be present in a composition of the present disclosure in a content ranging from 0.1% to 30% by weight of agents, such as from 0.5% to 20% by weight, relative to the total weight of the composition.

Thickeners

Depending on the fluidity of the composition that it is desired to obtain, one or more thickeners or gelling agents may be incorporated into a composition of the present disclosure.

A thickener or gelling agent suitable for the present disclosure may be hydrophilic, i.e. water-soluble or water-dispersible.

As hydrophilic gelling agents, mention may in particular be made of water-soluble or water-dispersible thickening polymers. Said polymers may in particular be selected from: modified or unmodified carboxyvinyl polymers, such as the products sold under the name Carbopol (CTFA name: carbomer) by the company Goodrich; polyacrylates and polymethacrylates, such as the products sold under the names Lubrajel and Norgel by the company Guardian or under the name Hispagel by the company Hispano Chimica; polyacrylamides; 2-acrylamido-2-methylpropanesulfonic acid polymers and copolymers, which are optionally cross-linked and/or neutralized, such as the poly(2-acrylamido-2-methylpropanesulfonic acid) sold by the company Clariant under the name "Hostacerin AMPS" (CTFA name: ammonium polyacryldimethyltauramide); crosslinked anionic acrylamide/AMPS copolymers, in the form of a W/O emulsion, such as those sold under the name Sepigel 305 (CTFA name: Polyacrylamide/C13-14 Isoparaffin/Laureth-7) and under the name Simulgel 600 (CTFA name: Acrylamide/Sodium acryloyldimethyltaurate copolymer/Isohexadecane/Polysorbate 80) by the company SEPPIC; polysaccharide biopolymers, such as xanthan gum, guar gum, carob gum, gum acacia, scleroglucans, chitin derivatives and chitosan derivatives, carrageenans, gellans, alginates, or celluloses such as microcrystalline cellulose, carboxymethylcellulose, hydroxymethylcellullose and hydroxypropylcellulose; and mixtures thereof.

A thickener or gelling agent suitable for the present disclosure may be lipophilic, it may be mineral or organic.

As lipophilic thickeners, mention may, for example, be made of modified clays, such as modified magnesium silicate (BENTONE GEL® VS38 from Rheox), modified hectorites such as hectorite modified with a $C_{10}$ to $C_{22}$ fatty acid ammonium chloride, for instance hectorite modified with distearyldimethylammonium chloride, for instance the product sold under the name BENTONE 38V® by the company Elementis or the product sold under the name "BENTONE 38 CE®" by the company Rheox or the product sold under the name BENTONE GEL V5 5V® by the company Elementis.

The polymeric organic lipophilic gelling agents are, for example, partially or totally crosslinked elastomeric organopolysiloxanes with a three-dimensional structure, such as those sold under the names KSG6®, KSG16® and KSG18® by the company Shin-Etsu, TREFIL E-505C® and TREFIL E-506C® by the company Dow-Corning, GRANSIL SR-CYC®, SR DMF10®, SR-DC556®, SR 5CYC Gel®, SR DMF 10 Gel® and SR DC 556 Gel® by the company Grant Industries and SF 1204® and JK 113® by the company General Electric, ethylcellulose, such as the product sold under the name ETHOCEL® by the company Dow Chemical; polyamide-type polycondensates resulting from condensation between a dicarboxylic acid containing at least 32 carbon atoms and an alkylene diamine, and in particular ethylene diamine, in which the polymer comprises at least one terminal carboxylic acid group esterified or amidified with at least one monoalcohol or one monoamine containing from 12 to 30 carbon atoms, and linear and saturated, and in particular ethylenediamine/stearyl dilinoleate copolymers such as the product sold under the name UNICLEAR 100 VG® by the company Arizona Chemical; galactomannans containing from one to six, and in particular from two to four, hydroxyl groups per monosaccharide, substituted with a saturated or unsaturated alkyl chain, such as guar gum alkylated with $C_1$ to $C_6$, and in particular $C_1$ to $C_3$, chains, and mixtures thereof. Block copolymers of "diblock", "triblock" or "radial" type, of the polystyrene/polyisoprene or polystyrene/polybutadiene type, such as those sold under the name LUVITOL HSB® by the company BASF, of the polystyrene/copoly(ethylene-propylene) type, such as those sold under the name KRATON® by the company Shell Chemical Co, or else of the polystyrene/copoly(ethylene-butylene) type, blends of triblock and radial (star) copolymers in isododecane, such as those sold by the company Penreco under the name VERSAGEL, for instance the mixture of butylene/ethylene/styrene triblock copolymer and of ethylene/propylene/styrene star copolymer in isododecane (VERSAGEL M 5960®).

Among the lipophilic gelling agents that can be used in a cosmetic composition of the present disclosure, mention may also be made of esters of dextrin and of a fatty acid, such as dextrin palmitates, in particular such as those sold under the names RHEOPEARL TL® or RHEOPEARL KL® by the company Chiba Flour, hydrogenated plant oils, such as hydrogenated castor oil, fatty alcohols, in particular $C_8$ to $C_{26}$, and more particularly $C_{12}$ to $C_{22}$ fatty alcohols, for instance myristyl alcohol, cetyl alcohol, stearyl alcohol and behenyl alcohol.

According to embodiments, a composition may comprise thickeners in a content with respect to active material of from 0.01% to 40% by weight, especially from 0.1% to 20% by weight, in particular from 0.3% to 15% by weight, relative to the total weight of the composition.

Colorants

A composition may also comprise at least one colorant.

A cosmetic composition in accordance with the present disclosure may advantageously incorporate at least one colorant selected from organic or inorganic colorants, in particular such as pigments or nacres conventionally used in cosmetic compositions, liposoluble or water-soluble coloring agents, materials with a specific optical effect, and mixtures thereof.

The term "pigments" should be understood to mean white or colored, inorganic or organic particles which are insoluble in an aqueous solution and are intended for coloring and/or opacifying the resulting film.

The pigments may be present in a proportion of from 0.1% to 40% by weight, such as from 1% to 30% by weight, or from 5% to 15% by weight, relative to the total weight of the cosmetic composition.

As inorganic pigments that can be used, mention may be made of titanium dioxide, zirconium oxide or cerium oxide, and also zinc oxide, iron oxide or chromium oxide, ferric blue, manganese violet, ultramarine blue and chromium hydrate.

The pigment may also be a pigment having a structure which may be, for example, of sericite/brown iron oxide/titanium dioxide/silica type. Such a pigment is sold, for example, under the reference Coverleaf NS or JS by the company Chemicals and Catalysts and has a contrast ratio of around 30.

The colorant may also comprise a pigment having a structure which may, for example, be of the type of silica microspheres containing iron oxide. An example of a pigment having this structure is sold by the company Miyoshi under the reference PC Ball PC-LL-100 P, this pigment being composed of silica microspheres containing yellow iron oxide.

Among the organic pigments that can be used, mention may be made of carbon black, D & C pigments, lakes based on cochineal carmine, on barium, strontium, calcium or aluminum, or else the diketopyrrolopyrroles (DPP) described in documents EP-A-542 669, EP-A-787 730, EP-A-787 731 and WO-A-96/08537.

The term "nacres" should be understood to mean iridescent or noniridescent colored particles of any shape, which are in particular produced by certain molluscs in their shell or else are synthesized, and which exhibit a color effect by optical interference.

The nacres may be selected from pearlescent pigments such as titanium mica coated with iron oxide, titanium mica coated with bismuth oxychloride, titanium mica coated with chromium oxide, titanium mica coated with an organic dye, and pearlescent pigments based on bismuth oxychloride. This may also involve mica particles at the surface of which are superposed at least two successive layers of metal oxides and/or of organic colorants.

By way of example of nacres, mention may also be made of natural mica coated with titanium oxide, with iron oxide, with natural pigment or with bismuth oxychloride.

Among the nacres available on the market, mention may be made of the nacres Timica, Flamenco and Duochrome (based on mica) sold by the company Engelhard, the Timiron nacres sold by the company Merck, the Prestige mica-based nacres sold by the company Eckart and the synthetic-mica-based Sunshine nacres sold by the company Sun Chemical.

The nacres may more particularly possess a yellow, pink, red, bronze, orange, brown, gold and/or copper color or glint.

By way of illustration of nacres which can be used in the context of the present disclosure, mention may in particular be made of the golden nacres sold in particular by the hcompany Engelhard under the name Brillant gold 212G (Timica), Gold 222C (Cloisonne), Sparkle gold (Timica), Gold 4504 (Chromalite) and Monarch gold 233X (Cloisonne); the bronze nacres sold in particular by the company Merck under the name Bronze fine (17384) (Colorona) and Bronze (17353) (Colorona) and by the company Engelhard under the name Super bronze (Cloisonne); the orange nacres sold in particular by the company Engelhard under the name Orange 363C (Cloisonne) and Orange MCR 101 (Cosmica) and by the company Merck under the name Passion orange (Colorona) and Matte orange (17449) (Microna); the brown-hued nacres sold in particular by the company Engelhard under the name Nu-antique copper 340XB (Cloisonne) and Brown CL4509 (Chromalite); the copper-glint nacres sold in particular by the company Engelhard under the name Copper 340A (Timica); the red-glint nacres sold in particular by the company Merck under the name Sienna fine (17386) (Colorona); the yellow-glint nacres sold in particular by the company Engelhard under the name Yellow (4502) (Chromalite); the gold-glint red-hued nacres sold in particular by the company Engelhard under the name Sunstone G012 (Gemtone); the pink nacres sold in particular by the company Engelhard under the name Tan opale G005 (Gemtone); the gold-glint black nacres sold in particular by the company Engelhard under the name Nu antique bronze 240 AB (Timica), the blue nacres sold in particular by the company Merck under the name Matte blue (17433) (Microna), the silver-glint white nacres sold in particular by the company Merck under the name Xirona Silver and the green-gold and pinkish orangish nacres sold in particular by the company Merck under the name Indian summer (Xirona), and mixtures thereof.

The cosmetic composition according to the present disclosure may also comprise water-soluble or liposoluble dyes. The liposoluble dyes are, for example, Sudan red, DC Red 17, DC Green 6, β-carotene, soya oil, Sudan brown, DC Yellow 11, DC Violet 2, DC orange 5 and quinoline yellow. The water-soluble dyes are, for example, beetroot juice and caramel.

The cosmetic composition according to the present disclosure may also contain at least one material with a specific optical effect.

This effect is different than a simple, conventional hue effect, i.e. a unified and stabilized effect of the kind produced by conventional colorants, such as, for example, monochromatic pigments. For the purpose of the present disclosure, the term "stabilized" signifies absence of an effect of variability of color with the angle of observation or else in response to a temperature change.

For example, this material may be selected from particles having a metallic glint, goniochromatic coloring agents, diffracting pigments, thermochromatic agents, optical brighteners, and also fibers, in particular of interference type. Of course, these various materials may be combined so as to provide the simultaneous manifestation of two effects, or even a new effect in accordance with the present disclosure.

The metallic-glint particles that can be used in the present disclosure are in particular selected from:

particles of at least one metal and/or of at least one metal derivative, particles comprising a single-substance or multi-substance, organic or inorganic substrate, at least partially coated with at least one metal-glint layer comprising at least one metal and/or at least one metal derivative, and mixtures of said particles.

Among the metals that may be present in said particles, mention may, for example, be made of Ag, Au, Cu, Al, Ni, Sn, Mg, Cr, Mo, Ti, Zr, Pt, Va, Rb, W, Zn, Ge, Te, Se and mixtures or alloys thereof, such as Ag, Au, Cu, Al, Zn, Ni, Mo, Cr and mixtures or alloys thereof (for example, bronzes and brasses).

The term "metal derivatives" denotes compounds derived from metals, in particular oxides, fluorides, chlorides and sulfides.

By way of illustration of these particles, mention may be made of aluminum particles, such as those sold under the names STARBRITE 1200 EAC® by the company Siberline and METALURE® by the company Eckart.

Mention may also be made of metal powders of copper or of alloy mixtures, such as the references 2844 sold by the company Radium Bronze, metal pigments, such as aluminum or bronze, for instance those sold under the name Rotosafe 700 by the company Eckart, the silica-coated aluminum particles sold under the name Visionaire Bright Silver from the company Eckart, and the metal alloy particles such as silica-coated bronze (copper and zinc alloy) sold under the name Visionaire Bright Natural Gold from the company Eckart.

The particles in question may also be particles comprising a glass substrate, such as those sold by the company Nippon Sheet Glass under the name Microglass Metashine.

The goniochromatic coloring agent may be selected, for example, from multilayer interference structures and liquid-crystal coloring agents.

Examples of symmetrical multilayer interference structures that may be used in compositions prepared in accordance with the present disclosure are, for example, the following structures: $Al/SiO_2/Al/SiO_2/Al$, pigments having this structure being sold by the company Dupont de Nemours; $Cr/MgF_2/Al/MgF_2/Cr$, pigments having this structure being sold under the name Chromaflair by the company Flex; $MoS_2/SiO_2/Al/SiO_2/MoS_2$; $Fe_2O_3/SiO_2/Al/SiO_2/Fe_2O_3$ and $Fe_2O_3/SiO_2/Fe_2O_3/SiO_2/Fe_2O_3$, pigments having these structures being sold under the name Sicopearl by the company BASF; $MoS_2/SiO_2/mica-oxide/SiO_2/MoS_2$; $Fe_2O_3/SiO_2/mica-oxide/SiO_2/Fe_2O_3$; $TiO_2/SiO_2/TiO_2$ and $TiO_2/Al_2O_3/TiO_2$; $SnO/TiO_2/SiO_2/TiO_2/SnO$; $Fe_2O_3/SiO_2/Fe_2O_3$; $SnO/mica/TiO_2/SiO_2/TiO_2/mica/SnO$, pigments having these structures being sold under the name Xirona by the company Merck (Darmstadt). By way of example, these pigments may be the pigments of silica/titanium oxide/tin oxide structure sold under the name Xirona Magic by the company Merck, the pigments of silica/brown iron oxide structure sold under the name Xirona Indian Summer by the company Merck and the pigments of silica/titanium oxide/mica/tin oxide structure sold under the name Xirona Carribean Blue sold by the company Merck. Mention may also be made of the Infinite Colors pigments from the company Shiseido. Depending on the thickness and the nature of the various layers, various effects are obtained. Thus, with the $Fe_2O_3/SiO_2/Al/SiO_2/Fe_2O_3$ structure, the color changes from green-golden to red-gray for $SiO_2$ layers of 320 to 350 nm; from red to golden for $SiO_2$ layers of 380 to 400 nm; from violet to green for $SiO_2$ layers of 410 to 420 nm; from copper to red for $SiO_2$ layers of 430 to 440 nm.

By way of example of pigments with a polymeric multilayer structure, mention may be made of those sold by the company 3M under the name Color Glitter.

Examples of liquid-crystal goniochromatic particles that may be used include those sold by the company Chenix, and also the product sold under the name HELICONE® HC by the company Wacker.

Fillers

A composition in accordance with the present disclosure may also comprise at least one filler, of organic or inorganic nature, which makes it possible in particular to confer thereon additional properties of mattness, of covering power and/or of improved stability with regard to exudation and post-application anti-migration properties.

The term "filler" should be understood to mean colorless or white solid particles of any shape, which are in a form that is insoluble or dispersed in the medium of the composition. Inorganic or organic in nature, they make it possible to confer body or rigidity on the composition, and/or softness, and uniformity on the makeup.

The fillers used in the compositions according to the present disclosure may be of lamellar, globular or spherical form, or in the form of fibers or in any other form intermediate between these defined forms.

The fillers may or may not be surface-coated, and in particular they may be surface-treated with silicones, amino acids, fluoro derivatives or any other substance that promotes the dispersion and compatibility of the filler in the composition.

Among the fillers that can be used in the compositions according to the present disclosure, mention may be made of talc, mica, kaolin, bentone, precipitated calcium carbonate, magnesium carbonate, magnesium hydrogen carbonate, hydroxyapatite, boron nitride, glass or ceramic microcapsules, composites of silica and of titanium dioxide, such as the TSG series sold by Nippon Sheet Glass, polyamide powders (NYLON® Orgasol from Atochem), poly-β-alanine powders and polyethylene powders, polytetrafluoroethylene powders (TEFLON®), lauroyllysine, starch, hollow polymer microspheres such as Expancel (Nobel Industrie), metal soaps derived from organic carboxylic acids having from 8 to 22 carbon atoms, such as from 12 to 18 carbon atoms, for example zinc stearate, magnesium stearate or lithium stearate, zinc laurate, magnesium myristate, POLYPORE® L 200 (Chemdal Corporation), silicone resin microbeads (for example, Tospearl® from Toshiba), polyurethane powders, in particular powders of crosslinked polyurethane comprising a copolymer, said copolymer comprising trimethylol hexyllactone. In embodiments, it may be a polymer of hexamethylene diisocyanate/trimethylol hexyllactone. Such particles are in particular commercially available, for example under the name PLASTIC POWDER D-400® or PLASTIC POWDER D-800® from the company Toshiki, and mixtures thereof.

Active Agents

A composition of the present disclosure may also comprise at least one cosmetic active agent and/or one dermatological active agent.

By way of nonlimiting examples of cosmetic and/or dermatological active agents suitable for the present disclosure, mention may be made of the active agents selected from the following agents:

hydrating agents, desquamating agents, barrier function enhancers, depigmenting agents, antioxidants, dermodecontracting agents, anti-glycation agents, agents for stimulating the synthesis of dermal and/or epidermal macromolecules and/or preventing their degradation, agents for stimulating fibroblast or keratinocyte proliferation and/or keratinocyte differentiation, agents for promoting maturation of the horny envelope, NO-synthase inhibitors, peripheral benzodiazepine receptor (PBR) antagonists, agents for increasing sebacious gland activity, agents for stimulating the energy metabolism of cells, tensioning agents, fat-restructuring agents, slimming agents, agents for promoting cutaneous microcirculation, calmatives and/or anti-irritants, sebum-regulated or antiseborrheic agents, astringents, cicatrizing agents, anti-inflammatories and anti-acne agents, matting agents, soft-focus fillers, fluorescent agents, agents for promoting the natural pinkish color of the skin, and abrasive or exfoliant fillers, and mixtures thereof.

The cosmetic and/or dermatological active agents suitable for the present disclosure may in particular be selected from the agents mentioned in application EP 1 847 247.

It is part of the abilities of those skilled in the art to select said active agent(s) and the content thereof as a function of the desired effect on the keratin materials, and so as not to affect the cosmetic properties of the compositions of the present disclosure.

By way of example, the active agent(s) may be present in a content ranging from 0.01% to 20% by weight, such as from 0.01% to 10%, or from 0.05% to 1% by weight of active agents, relative to the total weight of the composition.

Additives

A cosmetic composition according to the present disclosure may also further comprise any additive normally used in the field under consideration, for example selected from gums, anionic, cationic, amphoteric or nonionic surfactants, silicone surfactants, gums, resins, dispersants, semicrystalline polymers, antioxidants, essential oils, preservatives, fragrances, neutralizing agents, antiseptics, anti-UV protective agents, cosmetic active agents, such as vitamins, hydrating agents, emollients or collagen-protecting agents, and mixtures thereof.

Those skilled in the art can adjust the nature and amount of the additives present in the compositions in accordance with the present disclosure by means of routine operations, such that the cosmetic properties and the stability properties desired for these compositions are not thereby affected.

A composition according to the present disclosure may in particular be in the form of a composition for making up and/or caring for the skin or the lips, in particular a foundation.

The present invention is presented in greater detail in the examples described hereinafter, which are proposed only by way of illustration and should not be interpreted as limiting the invention.

EXAMPLES

Example 1

Influence of the Nature of the Polymer on Mattness Staying Power

The fluid foundation examples 1A (according to the invention) and 1B to 1D (comparative examples) show that the vinyl polymer having at least one carbosiloxane dendrimer-derived unit (1A) gives better results than the other polymers with respect to mattness staying power (1B, C, D).

| General formulation of example 1 | | |
|---|---|---|
| Phase | Compounds | % by weight |
| A1 | Cetyl PEG/PPG-10/1 dimethicone sold under the reference Abil EM 90 by the company Goldschmidt | 2.70 |
|  | Polyglycerol-4 isostearate sold under the reference Isolan GI 34 by the company Goldschmidt | 0.90 |
|  | Butyl paraben | 0.10 |
|  | Dimethicone copolyol sold under the reference KF 6017 by the company Shin Etsu | 3.00 |
| A2 | Cyclohexasiloxane | 8.95 |
| A3 | Bentone gel sold under the reference Bentone Gel VS 5 V by the company Elementis | 4.00 |
| A4 | POLYMER | X |
| A5 | Cyclohexasiloxane | 6.00 |
|  | Yellow iron oxide coated with aluminum stearoylglutamate | 1.79 |
|  | Red iron oxide coated with aluminum stearoylglutamate | 0.54 |
|  | Black iron oxide coated with aluminum stearoylglutamate | 0.19 |
|  | Titanium dioxide coated with aluminum stearoylglutamate | 7.48 |
|  | Nano titanium dioxide sold under the reference UV Titan M212 | 0.25 |
| A6 | ISODODECANE | Y |
| A7 | Silica microsphere sold under the reference SB 700 by the company Miyoshi Kasei | 5.50 |
| A8 | Frangrance | 0.30 |
| B | Demineralized water | 25.00 |
|  | Methyl paraben | 0.20 |
|  | PEG 20 | 1.70 |
|  | Magnesium sulfate | 0.70 |
|  | Phenoxyethanol | 0.70 |
| C | Ethanol | 5.00 |
|  | TOTAL | 100% |

|  | Example 1A (Invention) | Example 1B (comparative) | Example 1C (comparative) | Example 1D (comparative) |
| --- | --- | --- | --- | --- |
| Nature of the polymer | Copolymer of butyl acrylate containing dendritic silicone side chains: tri((trimethylsiloxy)siloxyethyldimethylsiloxy)silylpropyl-methacrylate in isododecane (40/60) sold under the reference Dow Corning FA 4002 ID by Dow Corning. | Trimethyl siloxysilicate resin sold under the reference SR 1000 by the company Momentive Performance Materials. | Copolymer of alkyl methacrylate containing silicone side chains in isododecane (40/60) sold under the reference KP 550 by the company Shin Etsu. | Copolymer of isobutyl methacrylate/bis hydroxypropyl dimethicone acrylate in isododecane (40/60) sold under the reference Granacrysil BMAS by the company Grant Industries. |
| % X of mixture (polymer + solvant) | 25.00 | 10.00 | 25.00 | 25.00 |
| % pure polymer | 10.00 | 10.00 | 10.00 | 10.00 |
| % isododecane | 15.00 | 0 | 15.00 | 15.00 |
| % Y of additional isododecane | 0 | 15.00 | 0 | 0 |
| Total X + Y | 25.00 | 25.00 | 25.00 | 25.00 |

Operating Protocol

The constituents of phase A1 are weighed out into the main beaker and heated to 75° C., until the butyl paraben has dissolved.

Phases A2 and A3 are then added, at ambient temperature, with stirring using a Moritz stirrer (1000 rpm). When the dispersion is completely homogeneous, phase A4 is added, while maintaining stirring.

Phase A5 is prepared separately by grinding, in a three-roll mill, a mixture of pigments and cyclohexasiloxane, three times.

This phase A5 is then added, while maintaining stirring, as are phases A6, A7 and A8.

Phase B, the aqueous phase, is also prepared separately, by weighing the PEG-20 out into a beaker, followed by the methyl paraben and the magnesium sulfate, and adding water preheated to 95° C.

The aqueous phase is stirred using a magnetic bar until the three constituents have dissolved, and then the phenoxyethanol is added at 40° C.

The emulsion is prepared at ambient temperature: phase B, the aqueous phase, is poured into the fatty phase with the stirring speed being gradually increased (Moritz stirrer) to 4500 rpm. The stirring is maintained for 10 min.

Next, phase C (ethanol) is finally added.

The product obtained is stirred in a Rayneri mixer (blade mixer) and stirred for 10 min at 100 rpm.

Measurement of the Mattness and of the Mattness Staying Power

The mattness and the mattness staying power are evaluated on a panel of 16 women according to the protocol previously indicated.

The results obtained with compounds A to D are given in the table below.

|  | Example 1A (Invention) | Example 1B (comparative) | Example 1C (comparative) | Example 1D (comparative) |
| --- | --- | --- | --- | --- |
| Mattness (Timm-T0) | +++ | +++ | +++ | +++ |
| Mattness staying power (T3h-Timm) | ++++ | ++ | ++ | ++ |

Mattness or mattness staying power:
+ weak,
++ medium,
+++ good,
++++ very good.

Example 2

Influence of the Nature of the Filler on Mattness Staying Power

The fluid foundation examples 2A and 2B, on the one hand, and 2E and 2D on the other hand, make it possible to show that silica gives better results than the other fillers with respect to the mattness staying power.

| General formulation of example 2 | | |
| --- | --- | --- |
| Phase | Compounds | % by weight |
| A1 | Cetyl PEG/PPG-10/1 dimethicone sold under the reference Abil EM 90 by the company Goldschmidt | 2.70 |
|  | Polyglycerol-4 isostearate sold under the reference Isolan GI 34 by the company Goldschmidt | 0.90 |
|  | Butyl paraben | 0.10 |
|  | Dimethicone copolyol sold under the reference KF 6017 by the company Shin Etsu | 3.00 |
| A2 | Cyclohexasiloxane | 8.95 |
| A3 | Bentone gel sold under the reference Bentone Gel VS 5 V by the company Elementis | 4.00 |
| A4 | Copolymer of butyl acrylate containing dendritic silicone side chains: tri((trimethylsiloxy)siloxyethyldimethylsiloxy)silylpropyl-methacrylate in isododecane (40/60) sold | 25.00 |

-continued

General formulation of example 2

| Phase | Compounds | % by weight |
|---|---|---|
| | under the reference Dow Corning FA 4002 ID by Dow Corning. | |
| A5 | Cyclohexasiloxane | 6.00 |
| | Yellow iron oxide coated with aluminum stearoylglutamate | 1.79 |
| | Red iron oxide coated with aluminum stearoylglutamate | 0.54 |
| | Black iron oxide coated with aluminum stearoylglutamate | 0.19 |
| | Titanium dioxide coated with aluminum stearoylglutamate | 7.48 |
| | Nano titanium dioxide sold under the reference UV Titan M212 | 0.25 |
| A6 | FILLER | 5.50 |
| A7 | Fragrance | 0.30 |
| B | Demineralized water | 25.00 |
| | Methyl paraben | 0.20 |
| | PEG 20 | 1.70 |
| | Magnesium sulfate | 0.70 |
| | Phenoxyethanol | 0.70 |
| C | Ethanol | 5.00 |
| | TOTAL | 100% |

Operating Protocol

The operating protocol is identical to that disclosed in example 1, with the exception of phase A8, which is absent in this second series of examples.

| | Example 2A (Invention) | Example 2B (Invention) | Example 2C (comparative) | Example 2D (comparative) |
|---|---|---|---|---|
| Nature of the filler | Silica microsphere sold under the reference SB 700 by the company Miyoshi Kasei | Silica microsphere sold under the reference SB 150 by the company Miyoshi Kasei | PMMA sold under the reference Micropearl M 100 by the company Matsumoto | Nylon 12 powder sold under the reference Orgasol 2002 EXD NAT COS by the company Arkema |
| Mattness (Timm-T0) | +++ | +++ | ++ | ++ |
| Mattness staying power (T3h-Timm) | ++++ | +++ | ++ | ++ |

Mattness or mattness staying power:
+ weak,
++ medium,
+++ good,
++++ very good

Example 3

Influence of the Amount of the Filler on Mattness Staying Power

The compositions of examples 3A and 3B show that the mattness staying power depends on the amount of the filler.

General formulation of example 3

| Phase | Compounds | % by weight |
|---|---|---|
| A1 | Cetyl PEG/PPG-10/1 dimethicone sold under the reference Abil EM 90 by the company Goldschmidt | 2.70 |
| | Polyglycerol-4 isostearate sold under the reference Isolan GI 34 by the company Goldschmidt | 0.90 |
| | Butyl paraben | 0.10 |
| | Dimethicone copolyol sold under the reference KF 6017 by the company Shin Etsu | 3.00 |
| A2 | Cyclohexasiloxane (D6) | 8.95 |
| A3 | Bentone gel sold under the reference Bentone Gel VS 5 V by the company Elementis | 4.00 |
| A4 | Butyl acrylate copolymer containing dendritic silicone side chains: Tri((trimethylsiloxy)siloxyethyldimethyl-siloxy)silylpropyl-methacrylate in isododecane (40/60) sold under the reference Dow Corning FA 4002 ID by Dow Corning | 25.00 |
| A5 | Cyclohexasiloxane (D6) | 6.00 |
| | Yellow iron oxide coated with aluminum stearoylglutamate | 1.79 |
| | Red iron oxide coated with aluminum stearoylglutamate | 0.54 |
| | Black iron oxide coated with aluminum stearoylglutamate | 0.19 |
| | Titanium dioxide coated with aluminum stearoylglutamate | 7.48 |
| | Nano titanium dioxide sold under the reference UV Titan M212 | 0.25 |
| A6 | Silica microsphere sold under the reference SB 700 by the company Miyoshi Kasei | X |
| A7 | Fragrance | 0.30 |
| B | Demineralized water | Y |
| | Methyl paraben | 0.20 |
| | PEG 20 | 1.70 |
| | Magnesium sulfate | 0.70 |
| | Phenoxyethanol | 0.70 |
| C | Ethanol | 5.00 |
| | TOTAL | 100% |

The operating protocol and the measurement of the mattness and of the mattness staying power are carried out as indicated for example 1.

| | Results: | |
|---|---|---|
| | Example 3A (Comparative) | Example 3B (Invention) |
| % X of silica | 0.3 | 5.5 |
| % Y of water | 30.20 | 25 |
| Mattness (Timm-T0) | +(+) | +++ |
| Staying power of the mattness (T3h-Timm) | ++ | ++++ |

Mattness or mattness staying power:
+ weak,
++ medium,
+++ good,
++++ very good

The obtained results show that the staying power of mattness of the comparative Example 3A (% of silica of 0.3%, i.e. <2%) is lower than the staying power of mattness of Example 3B according to the invention (% of silica of 5.5%, i.e. >2%).

Furthermore, the mattness of comparative Example 3A is lower than the mattness of Example 3B according to the invention.

The threshold of 2% for the amount of silica appears to be determinant for conferring to the compositions of the invention improved properties in terms mattness and of staying power of mattness.

The invention claimed is:

1. A cosmetic composition for making up and/or caring for the skin, comprising a physiologically acceptable medium containing:
   at least one vinyl polymer comprising at least one carbosioxane-dendrimer-derived unit, and
   from 2% to 15% by weight of a silica, relative to the total weight of the composition,
   with the proviso that said cosmetic composition is not a composition containing 21% by weight of cyclopentasiloxane, 4% by weight of a propylsisesquioxane wax substituted with alkyl units having at least 30 carbon atoms, 15% by weight of an acrylate/polytrimethylsiloxy methacrylate copolymer, 2% by weight of a cetyl PEG/PPG-10/1 dimethicone, 6% by weight of a dimethicone and dimethicone/polyglycerol-3 crosscopolymer, 3% by weight of silica, 1% by weight of nylon-12, 5% by weight of glycerol, 0.4% by weight of phenoxyethanol, 32.6% by weight of water and 10% by weight of a mixture of pigments formulated in cyclopentasiloxane;
   wherein, the at least one vinyl polymer having at least one carbosiloxane-dendrimer-derived unit is present in a content with respect to active material ranging from 2% to 20% by weight, relative to the total weight of the composition, with respect to active material of vinyl polymer having at least one carbosiloxane-dendrimer-derived unit, and
   wherein, the ratio by weight between said polymer and said silica is from 1 to 10.

2. The composition of claim 1, in which the at least one vinyl polymer comprising at least one carbosiloxane-dendrimer-derived unit has a side molecular chain containing a carbosiloxane dendrimer structure, and the at least one vinyl polymer is derived from a polymerization:

(A) of 0 to 99.9 parts by weight of a vinyl monomer; and
(B) of 100 to 0.1 parts by weight of a carbosiloxane dendrimer containing a radical-polymerizable organic group, represented by the general formula:

$$Y-Si \left[ O-Si-X^i \atop R^1 \right]_3 \atop R^1$$

in which Y represents a radical-polymerizable organic group,
$R^1$ represents an aryl group or an alkyl group having from 1 to 10 carbon atoms, and
$X^i$ represents a silylalkyl group which, when i=1, is represented by the formula:

$$X^i = -R^2-Si \left[ O-Si-X^{i+1} \atop R^1 \right]_{3-a^i} \atop R^1 \atop (OR^3)_{a^i}$$

in which $R^1$ is as defined above,
$R^2$ represents an alkylene group having from 2 to 10 carbon atoms,
$R^3$ represents an alkyl group having from 1 to 10 carbon atoms,
$X^{i+1}$ represents a hydrogen atom, an alkyl group having from 1 to 10 carbon atoms, an aryl group, or the silylalkyl group as defined above with i=i+1;
i is an integer from 1 to 10 which represents the generation of said silylalkyl, and
$a^i$ is an integer from 0 to 3;
where said radical-polymerizable organic group contained in the component (B) is selected from the group consisting of:
organic groups containing a methacrylic group or an acrylic group and which are represented by the formulae:

$$CH_2=C-C-O-R^6- \atop R^4 \quad O$$

and $$CH_2=C-C-NH-R^5- \atop R^4 \quad O$$

in which $R^4$ represents a hydrogen atom or an alkyl group,
$R^5$ represents an alkylene group having from 1 to 10 carbon atoms; and
organic groups containing a styryl group and which are represented by the formula:

$$CH_2=C-\underset{R^6}{\overset{}{\bigg|}}-\!\!\!\!\bigcirc\!\!\!\!-R^7_b \atop R^8_c$$

in which $R^6$ represents a hydrogen atom or an alkyl group,
$R^7$ represents an alkyl group having from 1 to 10 carbon atoms,
$R^8$ represents an alkylene group having from 1 to 10 carbon atoms,
b is an integer from 0 to 4, and
c is 0 or 1, such that, if c is 0, —$(R^8)_c$— represents a bond.

3. The composition as claimed in claim 1, in which the least one vinyl polymer having at least one carbosiloxane-dendrimer-derived unit is derived from a copolymerization:
   (A) of vinyl monomers containing organofluorine groups in the molecule,
   (B) optionally of vinyl monomers not containing any organofluorine groups in the molecule, and
   (C) of carbosiloxane dendrimers having radical-polymerizable organic groups represented by general formula (III):

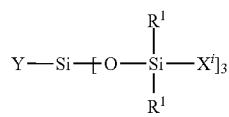

in which Y is a radical-polymerizable organic group,
$R^1$ is an aryl or alkyl group having from 1 to 10 carbon atoms, and
$X^i$ is a silylalkyl group represented by formula (II) below:

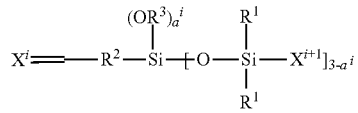

in which $R^1$ is as defined above,
$R^2$ is an alkylene group having from 1 to 10 carbon atoms,
$R^3$ is an alkyl group having from 1 to 10 carbon atoms, and
$X^{i+1}$ is a group selected from the group consisting of hydrogen atoms, aryl groups and alkyl groups having up to 10 carbon atoms, and silylalkyl groups $X^i$ mentioned above,
where i is an integer from 1 to 10 indicating the generation of said silylalkyl group beginning in each carbosiloxane dendritic structure with a value of 1 for the group X in formula (III), and
$a^i$ is an integer from 0 to 3,
said vinyl polymer having a copolymerization ratio of the component (A) to the component (B) of 0.1 to 100:99.9 to 0% by weight, and a copolymerization ratio of the sum of the component (A) and of the component (B) to the component (C) of 0.1 to 99.9:99.9 to 0.1% by weight.

4. The composition as claimed in claim 3, in which said radical-polymerizable organic group Y in the component (C) is a group selected from the group consisting of:
   organic groups containing acrylic or methacrylic groups represented by the general formula:

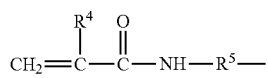

in which $R^4$ is a hydrogen atom or methyl, and
$R^5$ is an alkylene group having from 1 to 10 carbon atoms or

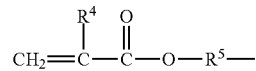

in which $R^4$ and $R^5$ are as defined above,
organic groups containing alkenylaryl groups represented by the general formula:

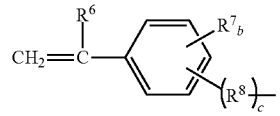

in which $R^6$ is a hydrogen atom or methyl,
$R^7$ is an alkyl group having from 1 to 10 carbon atoms,
$R^8$ is an alkylene group having from 1 to 10 carbon atoms,
b is an integer from 0 to 4 and
c is 0 or 1,
and alkenyl groups having from 2 to 10 carbon atoms.

5. The composition as claimed in claim 1, in which the at least one vinyl polymer having at least one carbosiloxane-dendrimer-derived unit comprises at least one tri[tri(trimethylsiloxy)silylethyldimethylsiloxy]silylpropyl carbosiloxane-dendrimer-derived unit, corresponding to one of the formulae:

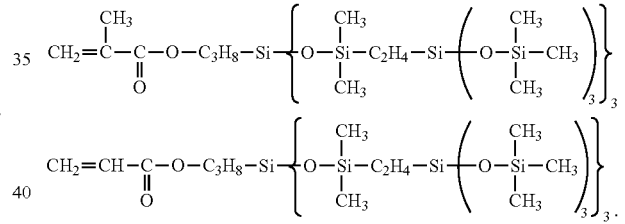

6. The composition as claimed in claim 1, in which said silica is a hydrophilic or hydrophobic silica selected from the group consisting of precipitated silicas, fumed silicas, and mixtures thereof.

7. The composition as claimed in claim 1, in which said silica is present in the form of particles having a mean size ranging from 5 nm to 25 μm.

8. The composition as claimed in claim 1, comprising at least one liquid fatty phase.

9. The composition as claimed in claim 1, comprising at least one lipophilic gelling agent.

10. The composition as claimed in claim 1, comprising at least one colorant.

11. The composition as claimed in claim 1, said composition being a foundation.

12. A nontherapeutic method for making up and/or caring for the skin, comprising at least one step of applying, to said skin, at least one layer of a composition as claimed in claim 1.

* * * * *